United States Patent [19]

McEwen

[11] Patent Number: 4,469,099
[45] Date of Patent: Sep. 4, 1984

[54] PNEUMATIC TORNIQUET

[75] Inventor: James A. McEwen, Richmond, Canada

[73] Assignee: Western Clinical Engineering Ltd., Vancouver, Canada

[21] Appl. No.: 451,610

[22] Filed: Dec. 20, 1982

Related U.S. Application Data

[63] Continuation of Ser. No. 193,145, Oct. 2, 1980, abandoned.

[51] Int. Cl.³ .............................................. A61B 17/12
[52] U.S. Cl. ..................................... 128/327; 128/682
[58] Field of Search ................ 128/327, 686, 691, 682

[56] References Cited

U.S. PATENT DOCUMENTS

| | | | |
|---|---|---|---|
| 3,552,383 | 1/1971 | Krueger et al. | 128/682 |
| 4,106,002 | 8/1978 | Hogue | 128/327 X |
| 4,294,261 | 10/1981 | Baker et al. | 128/327 X |
| 4,321,929 | 3/1982 | Lemelson et al. | 128/630 |

FOREIGN PATENT DOCUMENTS 1253501 11/1971 United Kingdom ................ 128/682

Primary Examiner—Michael H. Thaler
Attorney, Agent, or Firm—Klarquist, Sparkman, Campbell, Leigh & Whinston

[57] ABSTRACT

A pneumatic tourniquet includes an inflatable cuff, a pressurizing mechanism for pressurizing the cuff, a pressure relief mechanism for depressurizing the cuff, a pressure sensing mechanism for sensing the pressure to which the cuff is pressurized and a pressure regulator mechanism for selectably activating the pressurizing mechanism and the pressure relief means to maintain the cuff pressure near a selected pressure. Visual and audible alarm signals are triggered if the cuff pressure exceeds a cuff pressurization limit, if the cuff pressure falls below a cuff depressurization limit, or if the cuff has remained pressurized for, or in excess of a selected time period.

A computer may be used to sense the cuff pressure and pressurized or depressurized the cuff as required to maintain the cuff pressure within upper and lower cuff pressure limits.

11 Claims, 19 Drawing Figures

PNEUMATIC TORNIQUET

This application is a continuation of application Ser. No. 193,145, filed Oct. 2, 1980 now abandoned.

FIELD OF THE INVENTION

This invention pertains to pneumatic tourniquets for occluding blood flow into a limb while surgical procedures are performed on the limb. In particular, the invention pertains to pneumatic tourniquets having means for automatically sensing and controlling the pressure in an inflatable cuff which encircles the limb.

BACKGROUND OF THE INVENTION

Conventional pneumatic tourniquets typically provide an inflatable cuff which may be wrapped around a patient's limb, a source of compressed gas for pressurizing the cuff, a pressure gauge for measuring the cuff pressure, and a pressure regulating mechanism. Typically, the cuff is wrapped around the patent's limb and pressurized with compressed gas to a pressure as high as 650 mmHg in order to stop the flow of blood into the limb. A surgeon is thus provided with a "bloodless field" in which surgical procedures may be performed on the limb. The pressure gauge provides the operator with an indication of cuff pressure. The pressure regulating mechanism is intended to maintain cuff pressure relatively constant.

It has been estimated that about 10,000 conventional pneumatic tourniquets are currently used in about 100,000 surgical procedures performed annually in North America. Regrettably, the wide spread use of pneumatic (and non-pneumatic) tourniquets in surgery has been accompanied by continuing reports of limb paralysis, nerve damage and other injuries believed to be attributable to tourniquets. A survey of the literature indicates that such complications may result from four factors:

1. Excessive cuff pressure (which may lead to nerve compression and other damage at the cuff site).
2. Insufficient cuff pressure (which may lead to passive congestion or hemorrhagic infiltration of the nerve).
3. Excessive periods of application of a pressurized tourniquet to the limb.
4. Application of the tourniquet without consideration of the local limb anatomy.

Many reported cases of preventable nerve damage, limb paralysis and other injuries are believed to have resulted from the factors listed above, the most common of which appears to be overpressurization of the cuff [see: D. K. Wheeler and P. R. Lipscomb, A Safety Device for a Pneumatic Tourniquet, *J. Bone Joint Surg.*, 45A:870, 1964; W. K. Hamilton and M. D. Sokoll, Tourniquet Paralysis, *Journal of the American Medical Association*, 199:37, 1967; S. J. Prevoznik, Injury from Use of Pneumatic Tourniquets, *Anesthesiology*, 32:177, 1970; J. M. Bruner, Time, Pressure and Temperature Factors in the Safe Use of the Tourniquet, *Hand*, 2:39–42, 1970; D. Fry, Inaccurate Tourniquet Gauges, *Br. Med. J.*, 1:511, 1972; A. E. Flatt, Tourniquet Time in Hand Surgery, *Arch. Surg.*, 104:190–192, 1972; G. Burchell and G. Stack, Exsanguination of the Arm and Hand, *Hand*, 5:124–126, 1973]. Unfortunately, the actual incidence of tourniquet-induced complications in surgery may not be reliably estimated because the "tourniquet paralysis syndrome" (to borrow a phrase from J. Moldaver, Tourniquet Paralysis Syndrome, *Arch, Surg.* 68:136–144, 1954) may be difficult to detect or may be masked by the effects of surgery, because the damage is generally transient and reversible to a large extent and because such incidents may not be consistently reported due to concern over potential legal liability. (A hospital was recently found liable for nerve injuries suffered by a patient as a result of excessive pressure applied to her arm by a tourniquet ["Hospital Liable to Patient for Tourniquet Paralysis", *Citation*, 38:5, Oct. 15, 1978]).

Conventional tourniquets examined by the inventor which have been linked to possible nerve injuries or paralysis associated with cuff over-pressurization have been found to have malfunctioning pressure-regulating mechanisms or inherent hysteresis in the pressure-regulating mechanism which permitted the cuff pressure to rise about 150–400 mmHg above the desired cuff pressure (which is typically in the 200–650 mmHg range). Other tourniquets have been found to have aneroid pressure gauges which produced readings inaccurate by about 200 mmHg.

Attempts have been made to reduce injuries due to cuff over-pressurization by incorporating safety features into pneumatic tourniquets. For example, rocker valves of the type used in pressure cookers have been employed as pressure relief valves [see: Wheeler and Lipscomb (supra) and Hamilton and Sokoll (supra)]. However, limitations inherent in the technology of conventional pneumatic tourniquets appear to have prevented practical implementation of significant safety features. At best, rigorous operating, inspection and maintenance programs might be implemented in an effort to ensure that conventional tourniquets are used in a manner which would minimize potential cuff over or under pressurization and detect equipment malfunctions. However, implementation of such programs would likely be labour-intensive and could occupy a significant portion of the time available to an operating room nurse or technician.

An object of the present invention is to provide a pneumatic tourniquet capable of automatically sensing and regulating cuff pressure to maintain the cuff pressure near a selected pressure (for example, within about 6 mmHg of a pressure in the 200–400 mmHg range).

A related object is to provide a pneumatic tourniquet having automatic means for sensing cuff over-pressurization and triggering an appropriate alarm. For example, the cuff over-pressurization alarm might be triggered if the actual pressure in the cuff exceeds the selected cuff pressure by more than about 15 mmHg. A closely related object is the automatic triggering of a cuff under-pressurization alarm if, for example, the actual cuff pressure falls more than about 15 mmHg below the selected cuff pressure.

Conventional tourniquets typically do not provide a means for measuring the time period for which a pressurized tourniquet has been applied to a patient's limb. A pressurized conventional tourniquet might therefore be left on a patient's limb for a dangerously long period of time simply because operating room personnel may be occupied with other matters and overlook the time. Accordingly, a further related object is to provide a pneumatic tourniquet which triggers a time alarm if the cuff is inflated for, or in excess of a selected time period which will typically vary between about 0–180 minutes.

SUMMARY OF THE INVENTION

The invention is directed to a pneumatic tourniquet, comprising an inflatable cuff, pressurizing means for pressurizing the cuff, pressure relief means for depressurizing the cuff, pressure sensing means for producing a cuff pressure output signal representative of the pressure to which the cuff is pressurized, and pressure regulator means responsive to the cuff pressure output signal for selectably activating the pressurizing means and the pressure relief means to maintain the pressure to which the cuff is inflated near a selected pressure.

The pressure regulator means may comprise electronic sensing and control apparatus for comparing the cuff pressure output signal with a signal representative of the selected pressure, for producing a pressure decrease output signal to actuate the pressure relief means and depressurize the cuff if the cuff pressure exceeds an upper pressure limit and for producing a pressure increase output signal to actuate the pressurizing means and pressurize the cuff if the cuff pressure falls below a lower pressure limit. The pressure relief means may comprise a normally closed electronic pressure relief valve. The pressurizing means may comprise an electric air pump. Preferably, the pump is capable of pressurizing the cuff to a pressure no greater than about 500 mmHg. The pressure sensing means may comprise an electronic pressure transducer.

Advantageously, the cuff includes a first port for air passage into the cuff and a second port for air passage from the cuff. The pressurizing means and the pressure relief means may be coupled to the first port and the pressure sensing means may be coupled to the second port.

Preferably, the pneumatic tourniquet also comprises alarm means for producing a cuff over-pressurization alarm when the cuff pressure exceeds a cuff pressurization limit. The cuff pressurization limit may be about 15 mmHg greater than the selected pressure. Alarm means are also preferably provided for producing a cuff under-pressurization alarm when the cuff is depressurized below a cuff depressurization limit. The cuff depressurization limit may be about 15 mmHg less than the selected pressure. Time alarm means may also be provided for producing a time alarm when the cuff has remained inflated for, or in excess of a selected time period.

Alarm means may also be provided for producing a power alarm upon interruption of external power supplied to the pressurizing means, the pressure relief means, the pressure sensing means or the pressure regulator means. Advantageously, a battery is provided to supply power to at least the pressure sensing means upon interruption of the external power supply. Alarm means may be provided for producing a low battery alarm when the battery output voltage falls below a predetermined threshold.

BRIEF DESCRIPTION OF THE DRAWINGS

FIG. 5E illustrates the interconnection of those portions of the circuitry which are shown separately in FIGS. 5A through 5D.

FIG. 6C illustrates the interconnection of those portions of the circuitry which are shown separately in FIGS. 6A and 6B.

DESCRIPTION OF THE PREFERRED EMBODIMENT

I. Introduction

Figure 1:
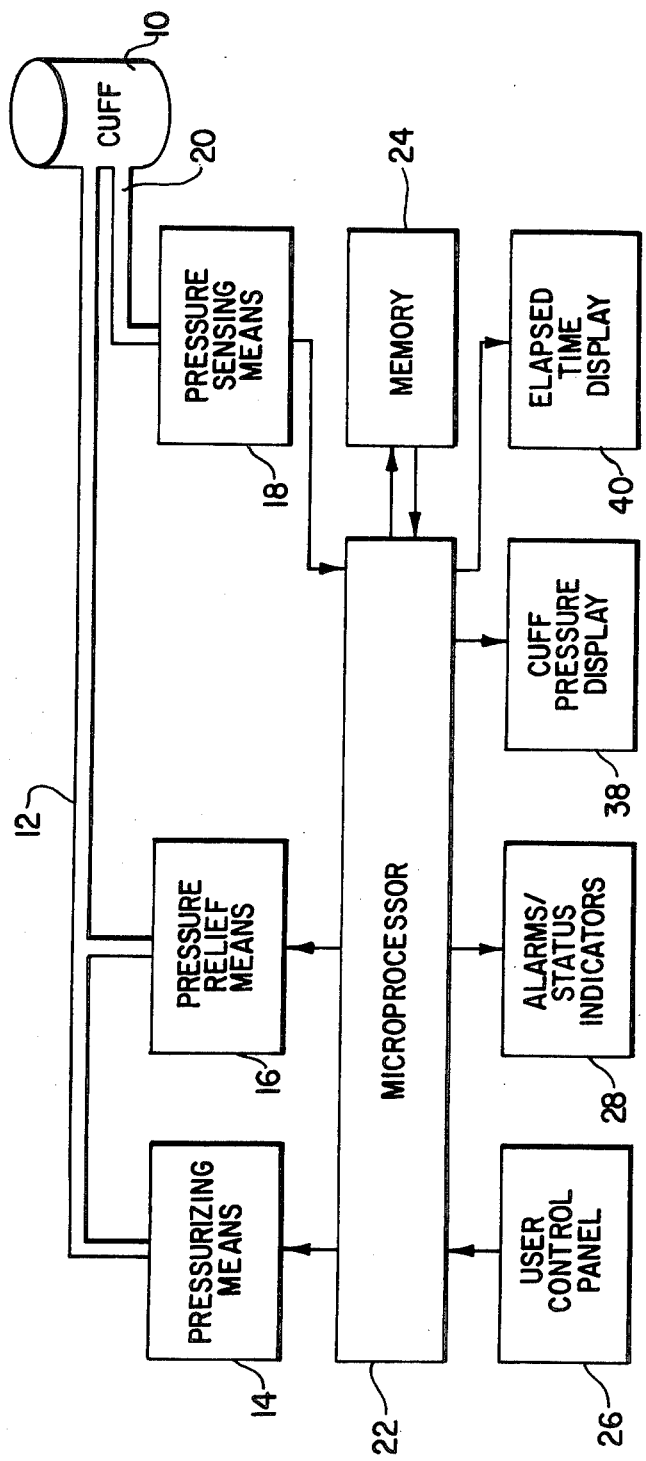
FIG. 1 is a block diagram of the preferred embodiment.

FIG. 1 is a block diagram which illustrates the operation of the preferred embodiment. An inflatable tourniquet cuff 10 which may be wrapped around a patient's limb is coupled via hose 12 to a pressurizing means 14 such as an electric air pump. Hose 12 is also coupled to a pressure relief means 16 such as a normally closed valve which may be electronically opened to depressurize cuff 10. A pressure sensing means 18 such as an electronic pressure transducer is coupled via hose 20 to a second port of cuff 10.

Pressurizing means 14, pressure relief means 16 and pressure sensing means 18 are electronically coupled to microprocessor 22 which has an associated memory 24.

A user control panel 26 is provided to enable the selection of various operating parameters. For example, a user may, with the aid of control panel 26, define a selected pressure to which cuff 10 is to be pressurized and a time period during which it is desired to maintain cuff 10 at or near the selected pressure.

Pressure sensing means 18 produces a cuff pressure output signal which is representative of the pressure in cuff 10. Microprocessor 22 is pre-programmed (as hereinafter described) to compare the cuff pressure output signal with a signal representative of the selected cuff pressure and to selectably activate either pressure relief means 16 (if the cuff pressure exceeds an upper pressure limit) or pressurizing means 14 (if the cuff pressure falls below a lower pressure limit) to maintain the pressure in cuff 10 near the selected pressure. In the preferred embodiment, the upper pressure limit is about 6 mmHg above the selected pressure and the lower pressure limit is about 6 mmHg below the selected pressure. Microprocessor 22 is also pre-programmed to monitor the cuff pressurization time period.

A number of alarm/status indicators 28 provide the operator with information respecting the operating status of the pneumatic tourniquet as well as visual and audible alarms to warn the operator of hazardous conditions such as over or under pressurization of the cuff. Visual and audible alarms are also triggered if cuff 10 remains pressurized for, or in excess of the selected cuff pressurization time period. The operator is provided with a digital readout of the instantaneous cuff pressure at cuff pressure display 38 and of the elapsed time during which the cuff has been pressurized at elapsed time display 40.

The preferred embodiment will first be described from the point of view of a typical user such as an operating room nurse or technician. A technical description of the construction and operation of the preferred embodiment will then be provided, followed by a discussion of the software programming for the microprocessor used in the preferred embodiment.

II. Operation by Nurse or Technician

Figure 2:
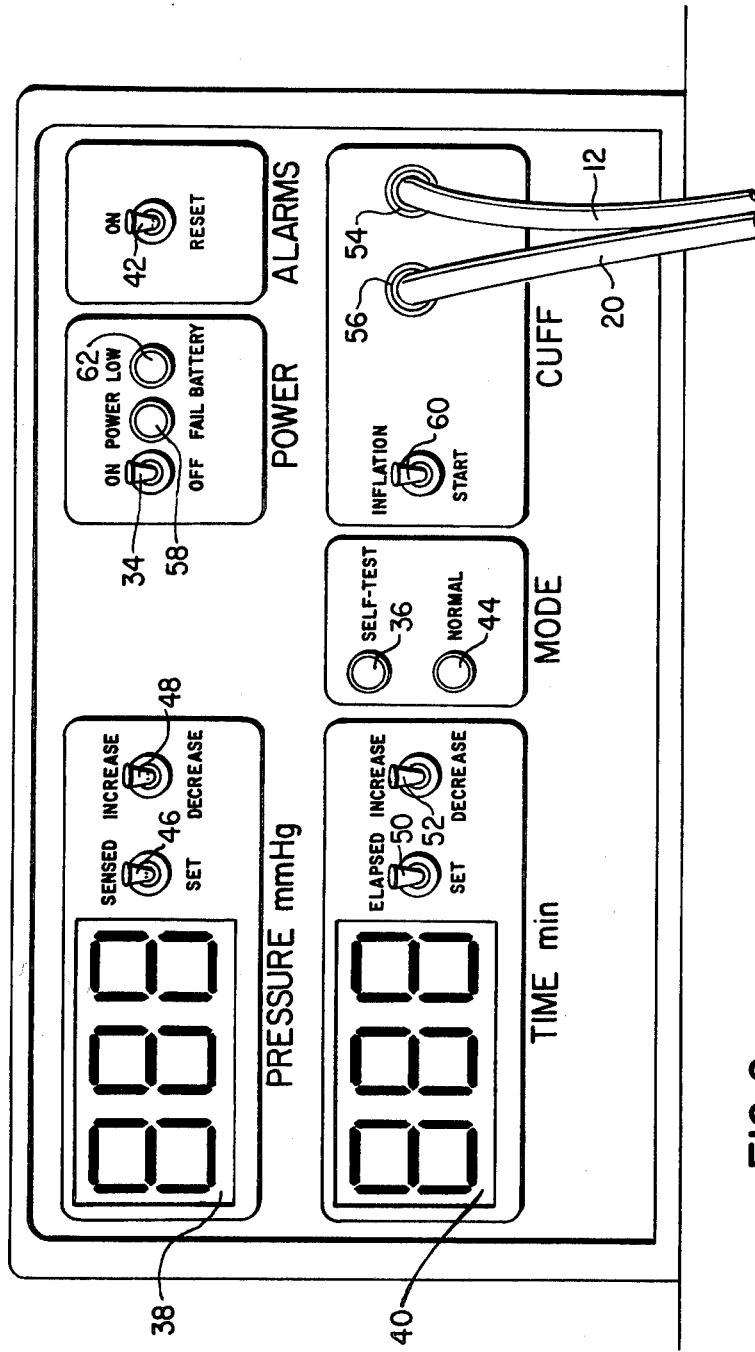
FIG. 2 is a pictorial representation of a control/display panel for the preferred embodiment.

FIG. 2 shows a control/display panel for the pneumatic tourniquet. The AC power plug (not shown) of the device is connected to an AC power receptacle and on/off power switch 34 is turned "on" to activate the pneumatic tourniquet. When switch 34 is turned "on" the pneumatic tourniquet automatically enters a "self-test" mode of operation which is indicated by the illumination of light 36. The self-test mode of operation enables the operator to verify that the device is operating properly.

(a) Self Test Mode of Operation

In the self-test mode, pressure display 38 and time display 40 (which are each three digit 7-segment light emitting diode displays) are each caused to display the numerals "888" so that the operator may verify that all display segments are functioning. An audible alarm (not shown in FIG. 2) is also sounded so that the operator may verify that it is working properly.

The operator should then disconnect the AC power plug from the receptacle and ensure that power fail light 58 is thereby illuminated. The AC plug is then reconnected which should extinguish indicator light 58.

Once the operator has verified the correct operation of displays 38 and 40, power fail indicator light 58 and the audible alarm he may momentarily depress switch 42 to the "reset" position to terminate the self-test sequence and enter the "normal" mode of operation (switch 42 normally remains in the "on" position depicted in FIG. 2). When the normal mode of operation is entered indicator light 36 is extinguished and indicator light 44 is illuminated.

(b) Normal Mode of Operation

The operator first selects the pressure to which cuff 10 is to be pressurized and the cuff pressurization time period.

To select the cuff pressure, the operator depresses switch 46 to the "set" position shown in FIG. 2. A pre-selected nominal pressure of 200 mmHg will appear in display 38. While continuing to depress switch 46, the operator may then either raise or lower the selected cuff pressure with respect to the nominal 200 mmHg level by moving switch 48 to the "increase" position (if a selected pressure greater than 200 mmHg is desired) or to the "decrease" position (if a selected pressure less than 200 mmHg is desired). When switch 48 is in the "increase" position, the pressure appearing in display 38 will gradually increase to a maximum of 400 mmHg. When switch 48 is in the "decrease" position, the pressure appearing in display 38 will gradually decrease to a minimum of 0 mmHg. When the selected cuff pressure appears in display 38, switch 46 is released. Note that two separate switches must be operated to select the cuff pressure. This is a safety feature intended to prevent inadvertent alteration of the selected cuff pressure. When switch 46 is released it returns to the "sensed" position, and display 38 provides the operator with a continual digital readout of the pressure to which cuff 10 is pressurized (initially, this will be "0").

The cuff pressurization time period is selected in similar fashion. Switch 50 is depressed to the "set" position shown in FIG. 2 and a pre-selected nominal time period of 60 minutes appears in display 40. While continuing to depress switch 50, the operator may either increase or decrease the cuff pressurization time period with respect to the nominal 60 minute time period by moving switch 52 to the "increase" position (if it is desired that the cuff remain pressurized for a period in excess of 60 minutes) or to the "decrease" position (if it is desired to pressurize the cuff for a period of time less than 60 minutes). In either case, the time presented in minutes at display 40 will gradually increase (to a maximum of 180 minutes) or decrease (to a minimum of 0 minutes). When the selected time period appears in display 40, the operator releases switches 50 and 52. Again, as a safety feature, two separate switches are required to set the cuff pressurization time period to avoid inadvertent alteration thereof. When switch 50 is released it returns to the "elapsed" position and display 40 provides the operator with a continual digital readout of the time period during which cuff 10 has remained pressurized to a pressure at or near the selected pressure (initially, a time period of "0" is displayed).

The patient's limb is prepared and cuff 10 applied thereto in accordance with established medical procedures.

Hose 12 couples an air inlet port of cuff 10 to pressurizing means 14 and to pressure relief means 16 via port 54 shown in FIG. 2. Hose 20 couples an air outlet port of cuff 10 to pressure sensing means 18 via port 56 shown in FIG. 2. [Preferably, separate supply and return hoses are used to convey pressurized air to and from cuff 10. Such a "dual-line" cuff may facilitate the detection of "kinks" or occlusions in the hoses. However, if a conventional single-port cuff must be used then an appropriate "Y" type adaptor should be used to couple a single hose from the cuff to ports 54 and 56.]

Once the cuff pressure and cuff pressurization time period have been selected, switch 60 is momentarily depressed to the "start" position to actuate pressurizing means 14 and pressurize cuff 10. Instantaneous values of cuff pressure in mmHg appear in display 38. Once cuff 10 has been pressurized to within 6 mmHg of the selected cuff pressure an elapsed-time clock is automatically activated to "count" the cuff pressurization time period, and instantaneous values of elapsed time (in minutes) appear in display 40. The device automatically regulates cuff pressure (as hereinafter described) to maintain it within about 6 mmHg of the selected cuff pressure. The preferred embodiment of the invention utilizes for each selected cuff pressure level a 6 mmHg pressure tolerance window within which the pressure regulator means regulates the cuff pressure. The 6 mmHg pressure tolerance window, therefore, shifts automatically in response to a change in selected cuff pressure.

To deflate cuff 10 upon completion of the medical procedure switches 46 and 48 are used to set the selected cuff pressure to a "zero" value. Cuff 10 then deflates to zero pressure as soon as switch 46 is released. Once cuff 10 has deflated switch 34 should be moved to the "off" position and cuff 10 removed from the patient.

(c) Alarms

Five separate alarms are provided, each of which may be triggered when the device is in the normal mode of operation to warn of potentially hazardous conditions.

A cuff over-pressurization alarm is triggered if the cuff pressure exceeds a cuff pressurization limit which, in the preferred embodiment, is 15 mmHg above the selected pressure. A cuff under-pressurization alarm is triggered if the cuff pressure falls below a cuff depressurization limit which, in the preferred embodiment, is 15 mmHg below the selected pressure. In either case, an audible alarm is sounded and display 38 flashes off and on to draw the operator's attention to the over or under-pressurization value which will appear in display 38. The audible pressure alarm may be temporarily deactivated by depressing switch 42 to the "reset" position. This action will deactivate the audible alarm for 30 seconds but display 38 will continue to flash.

If either the cuff over or under-pressurization alarms are triggered then the operator should examine hoses 12 and 20 for kinks or occlusions which may prevent free passage of pressurized air to and from cuff 10. Cuff 10, hoses 12 and 20 and the various connectors should also be checked for damage, leaks or obstructions. Both alarms are automatically deactivated upon correction of the condition which triggered the alarm.

A time alarm is triggered if cuff 10 remains inflated for, or in excess of the selected cuff pressurization time period. If the time alarm is triggered the audible alarm sounds and display 40 flashes on and off to draw the operator's attention to the excess period of cuff pressurization. The cuff is not depressurized. To deactivate the time alarm in order to complete a procedure the operator may increase the cuff pressurization time period to a new value up to a maximum of 180 minutes from commencement of the "count". The time alarm may be temporarily deactivated by depressing switch 42 to the "reset" position. This action will deactivate the audible alarm for 30 seconds but display 40 will continue to flash.

A power fail alarm is triggered upon interruption of external AC power supplied to the device. If AC power is interrupted the audible alarm sounds and indicator light 58 is illuminated. In the event of an AC power failure, an internal battery is automatically used to supply power to at least pressure sensing means 18 and the electronic circuitry so that the operator may continue to monitor the cuff pressure and the elapsed time. The power fail alarm is automatically deactivated upon reconnection of AC power to the device. The audible alarm which signals a failure of AC power may also be temporarily deactivated for 30 seconds by depressing switch 42 to the "reset" position.

A low battery alarm is triggered, sounding the audible alarm and illuminating indicator light 62 if the voltage of an internal backup battery falls below a predetermined threshold (which, in the preferred embodiment, is 10.2 volts) indicating that the battery may be able to power the device for only a short period of time. If the low battery alarm is triggered the device should immediately be connected to an AC power source to recharge the battery. The low battery alarm is automatically deactivated once the battery has been recharged.

Figure 3:
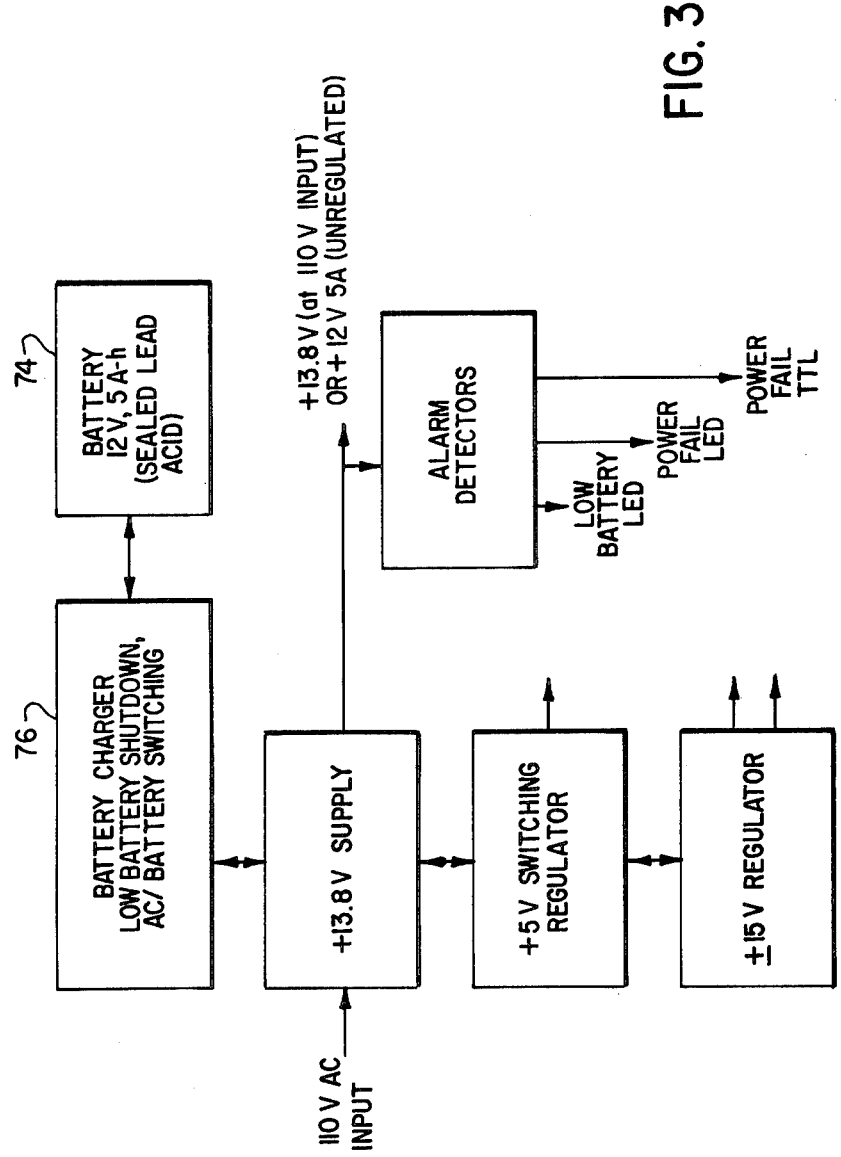
FIG. 3 is a block diagram of a power supply for the preferred embodiment.

III. Construction and Technical Operation (a) Power Supply and Backup Battery FIG. 3 depicts the power supply, backup battery and battery charger in block diagram form. The power supply converts an externally supplied 110 volt AC input signal into DC outputs of +13.8 volts (or +12 volts of unregulated power if the backup battery is used), +5 V, 15 V, and −15 V.

Battery 74 is a 12-volt, 5 amp-hour battery of the sealed lead-acid type. A charging circuit 76 is provided to maintain the voltage across the terminals of battery 74 at about +13.8 volts when the device is connected to a 110 volt AC power source.

Figure 4:
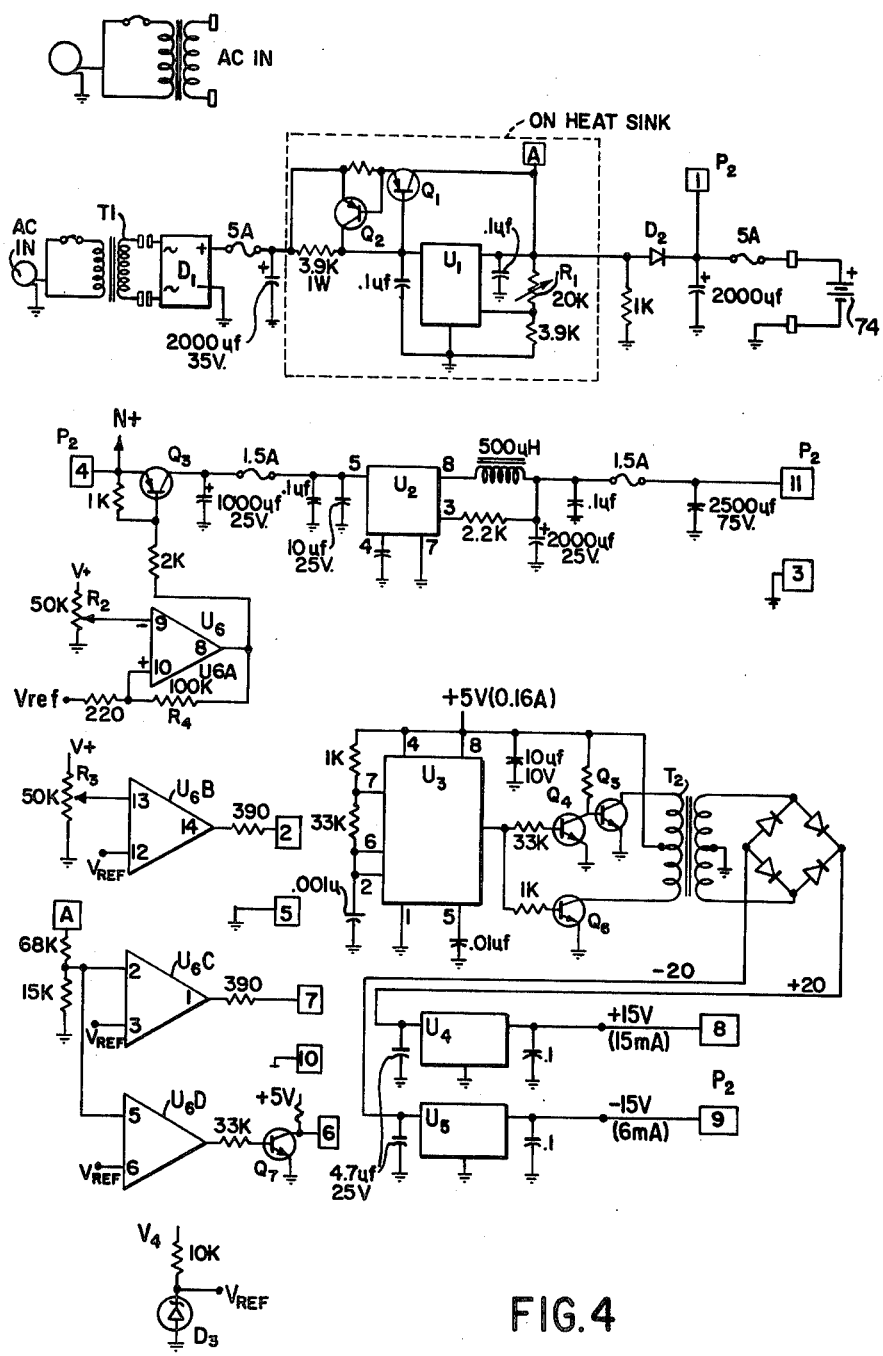
FIG. 4 is an electronic circuit schematic diagram of a power supply, backup battery and battery charging circuit for the preferred embodiment.

FIG. 4 is an electronic circuit schematic diagram of the power supply circuit, backup battery and battery charging circuitry.

Transformer T1 steps the 110 volt AC supply voltage down to 16 volts which is then rectified by diode bridge rectifier D1. Voltage regulator U1 and pass transistor Q1 regulate the voltage to +13.8 volts for presentation at the terminals of battery 74. Transistor Q2 limits the current applied to battery 74 to approximately 3 amps to avoid overcharging the battery. Diode D2 prevents battery current flowing back into voltage regulator U1. Variable resistor R1 is used to adjust the voltage at the terminals of battery 74 to +13.8 volts when a 110-volt AC power supply signal is presented at the input terminals of transformer T1. A battery charging voltage of +13.8 volts permits each cell of battery 74 to be charged at a constant voltage of 2.3 volts. A regulated source of +13.8 volts is thus available at pin 1 of connector P2 if a 110-volt AC input signal is presented at the input terminals of transformer T1. If an AC input signal is not present then +12 volts of unregulated power (derived from battery 74) is provided at pin 1 of connector P2. Pin 1 of connector P2 is coupled to pin 4 of connector P2 to supply power to other portions of power supply circuit 64.

Switching regulator U2 provides high efficiency step-down regulation of the +13.8 volt (or +12 volt) supply signal to +5 volts. The +5 volt signal is used to power the microprocessor 78 and its associated memories, as well as the analog to digital converter, timer, display drivers, solid state relays, indicator lights and audible alarm, all of which are hereinafter described.

Oscillator U3 and transistors Q4, Q5 and Q6 drive a step-up toroidal transformer T2 at 20 kHz. The secondary output of transformer T2 is rectified and regulated to 15 volts and −15 volts by voltage regulators U4 and U5 respectively. The +15 volt and −15 volt supplies are used to power pressure sensing means 18 and its associated processor circuitry (hereinafter described).

A quad operational amplifier U6 is used in a voltage comparator mode to provide "low battery", "power fail" and "battery shut-down" signals. A temperature compensated high precision reference diode D3 provides a voltage reference for the voltage comparators.

Variable resistor R2 is adjusted to shut off the driving signal presented by voltage comparator U6A to switching Darlington transistor Q3 if the voltage at the output terminals of battery 74 falls below the threshold of 10.2 volts. Q3 will thus disconnect battery 74 to prevent it from completely discharging. Resistor R4 adds a slight hysteresis to avoid operating transistor Q3 in its linear region.

Variable resistor R3 is adjusted so that voltage comparator U6B will produce a "low battery" output signal if the voltage across the terminals of battery 74 falls below a threshold of 11.4 volts. This signal is used to drive indicator light 62 shown in FIG. 2.

Voltage comparators U6C and U6D are used to detect the absence of the 110 volt externally supplied AC power signal, to drive "power fail" indicator light 58 shown in FIG. 2 and to provide a TTL logic signal suitable for input to the microprocessor as hereinafter described.

The following parts list provides details of components used in constructing the power supply shown in FIG. 4. All resistors and capacitors not listed below are standard components with values as shown on the schematic.

| ITEM | DESCRIPTION | QUANTITY |
|---|---|---|
| Circuit breaker | Potter & Brumfield 37-401-101 | 1 |
| $D_1$ | Motorola MDA-970-21 | 1 |
| Battery | Gates 2V, 5A-h, 0800-0004 | 6 |
| $D_2$ | Motorola 1N5402 | 1 |
| $Q_1, Q_2$ | Motorola MJE2955 | 2 |
| $Q_3$ | Motorola TIP 126 | 1 |
| $Q_4, Q_5, Q_6$ | Motorola 2N3904 | 3 |
| $Q_7$ | Motorola 2N4123 | 1 |
| $T_1$ | Hammond 166M16 | 1 |
| $T_2$ | Toroid, ⅞" OD, 50T/260T, #26 AWG | 1 |
| $U_1$ | Fairchild uA78G | 1 |
| $U_2$ | Fairchild SH1605 | 1 |
| $U_3$ | Motorola MC1455 | 1 |
| $U_4$ | Motorola 78L15 | 1 |
| $U_5$ | Motorola 79L15 | 1 |
| $U_6$ | National LM324 | 1 |
| $D_3$ | National LM113H | 1 |

(b) Pressurizing Means In the preferred embodiment, pressurizing means 14 comprises a WISA model 300 airpump. This is a solenoid/diaphragm pressure generator which operates from an AC 110 volt 60 Hz power supply and consumes about 5 watts. The pump is capable of generating a maximum cuff pressure of about 500 mmHg. This is a safety feature, as it has been suggested that cuff pressures no greater than about 400 mmHg should be adequate to maintain a bloodless surgical field. [See: L. Klenerman and G. H. Hulans, Tourniquet Pressures for the Lower Limb, *J. Bone Joint Surg.,* 61B:124, 1979; and, R. Sanders, The Tourniquet: Instrument or Weapon? *Hand,* 5:119-123, 1973]. Actuation of pressurizing means 14 by the microprocessor is discussed below under the heading "microprocessor and digital circuitry".

A Clippard EV-3 normally closed 3 way poppet valve (not shown) is placed in hose 12 between the pump and cuff 10 to protect the pump diaphragm from damage which may be caused by the air pressure in hose 12. When the pump is activated, the valve is electronically actuated to couple the pump to cuff 10 so that pressurized air may enter cuff 10. When the pump is deactivated the valve is actuated to seal hose 12 (thus preventing air escaping from cuff 10) and to couple the pump outlet port to atmosphere (thus relieving any back pressure on the pump diaphragm).

(c) Pressure Relief Means

In the preferred embodiment, pressure relief means 16 comprises a Clippard EVO-3-12 electronic valve. This is a normally open, 3-way poppet valve having a poppet travel of 0.010 inches, pressure range of 0-105 psi, air flow of 0.5 cfm. at 100 psi., and a response time of 5 ms at 100 psi. A +12 volt DC signal is used to actuate the valve which consumes about 0.65 watts at its rated pressure. Actuation of pressure relief means 16 by the microprocessor is discussed below under the heading "microprocessor and digital circuitry".

(d) Pressure Sensing Means

Figure 5A:
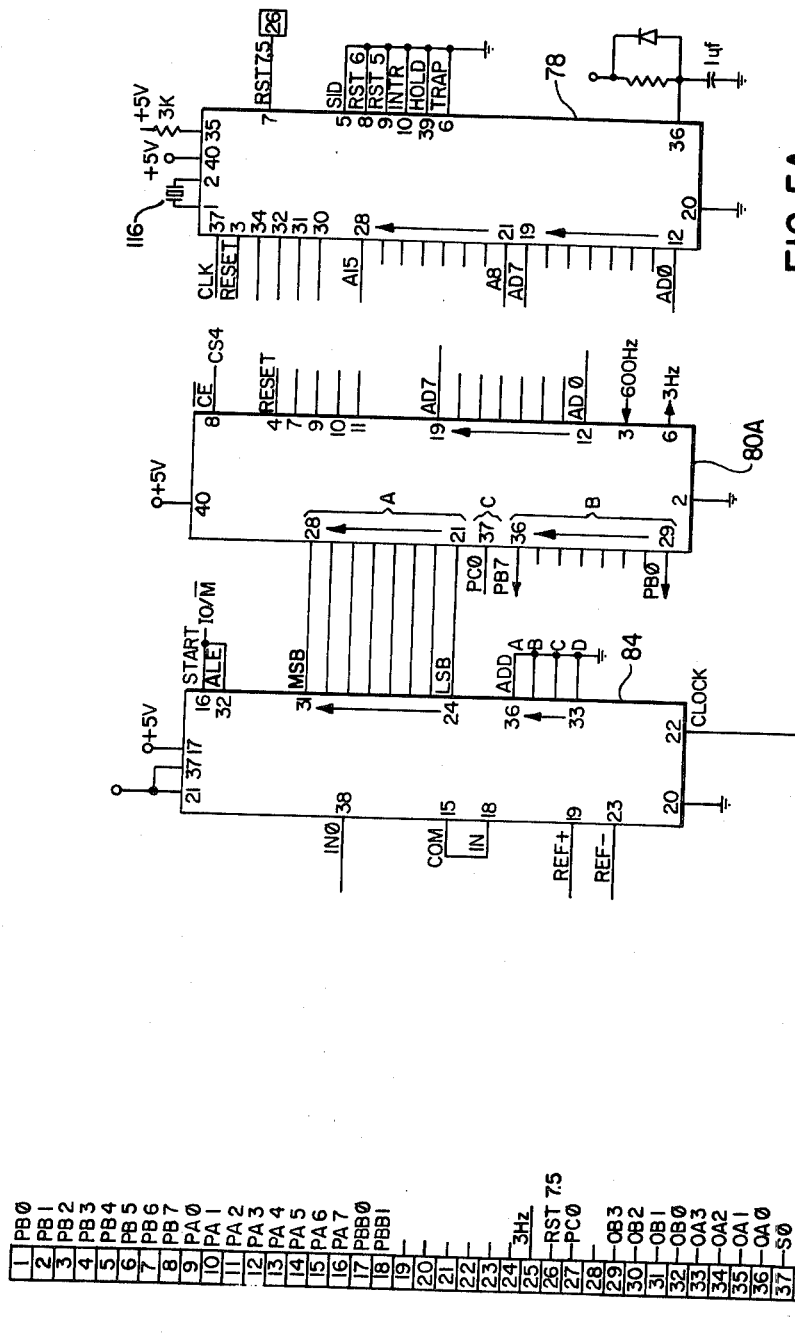
FIGS. 5A through 5D are an electronic circuit schematic diagram for the microprocessor and related circuitry which controls the preferred embodiment.
Figure 5B:
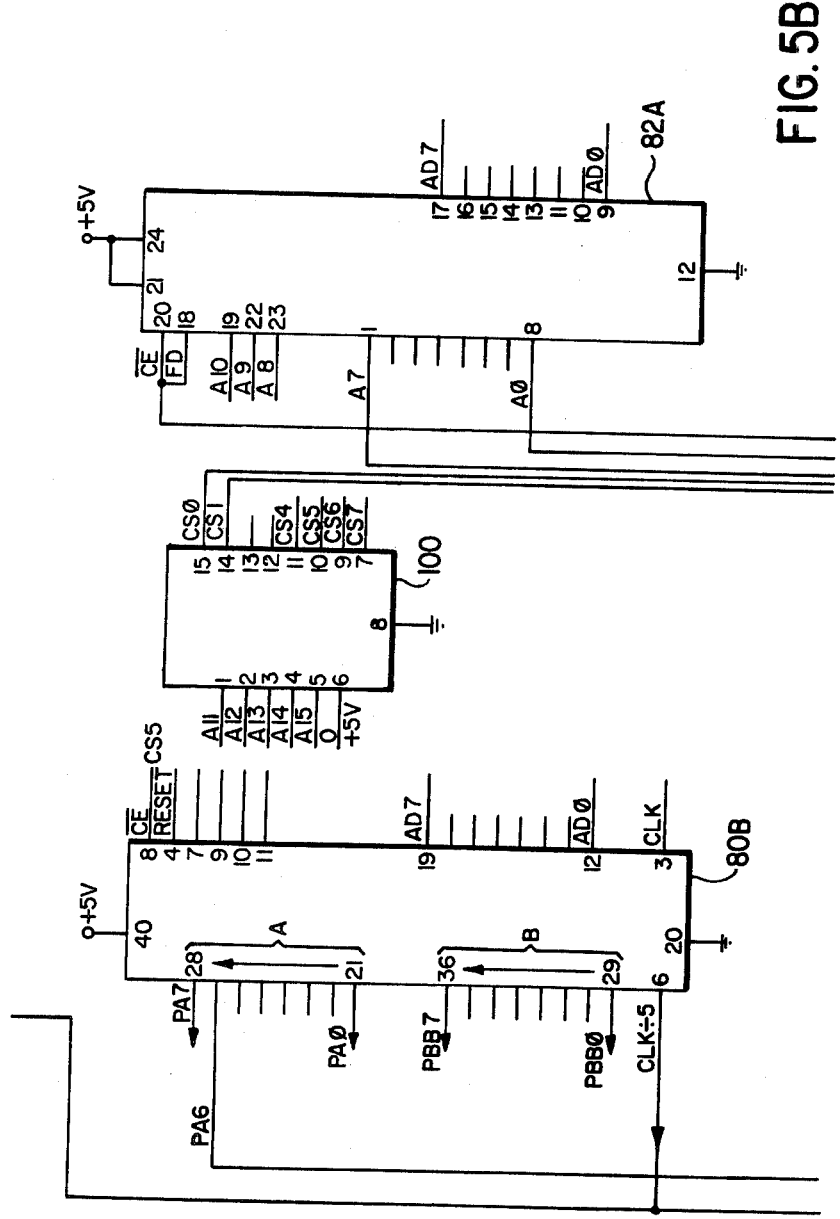
Figure 5C:
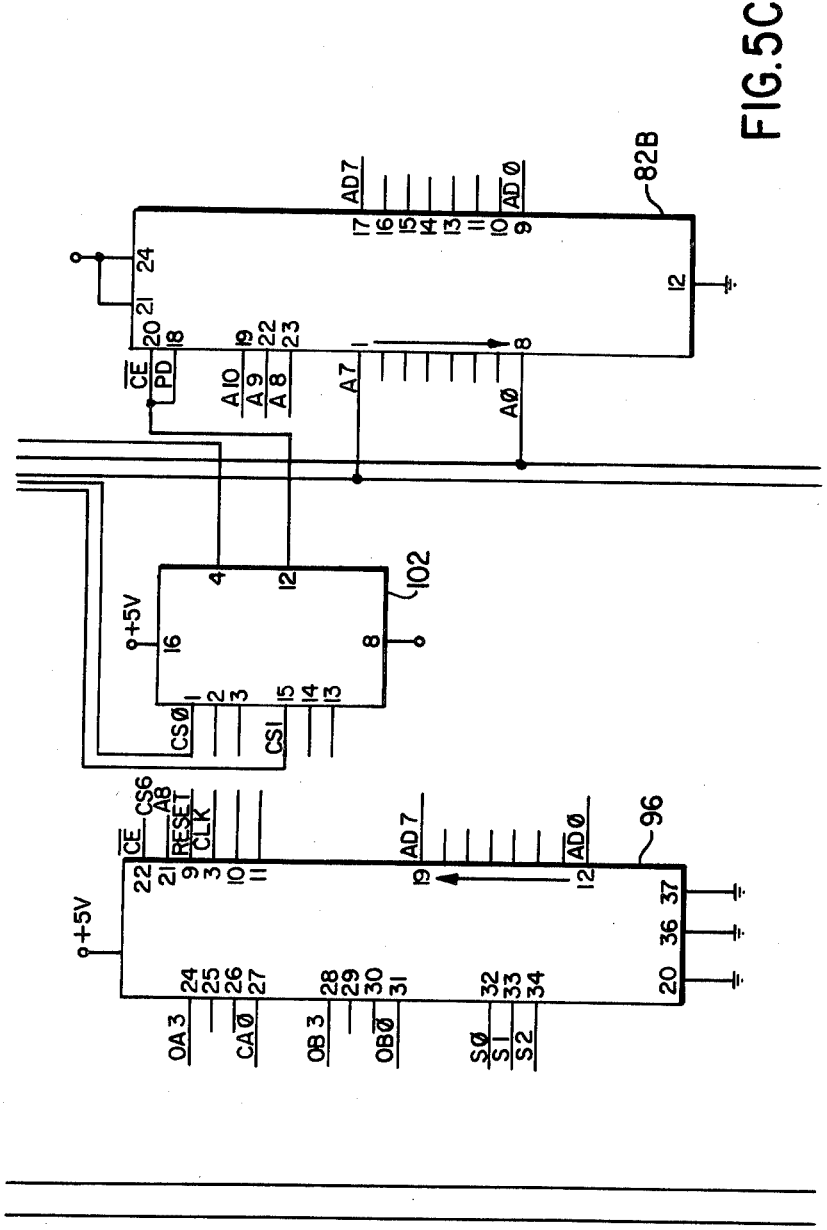
Figure 5D:
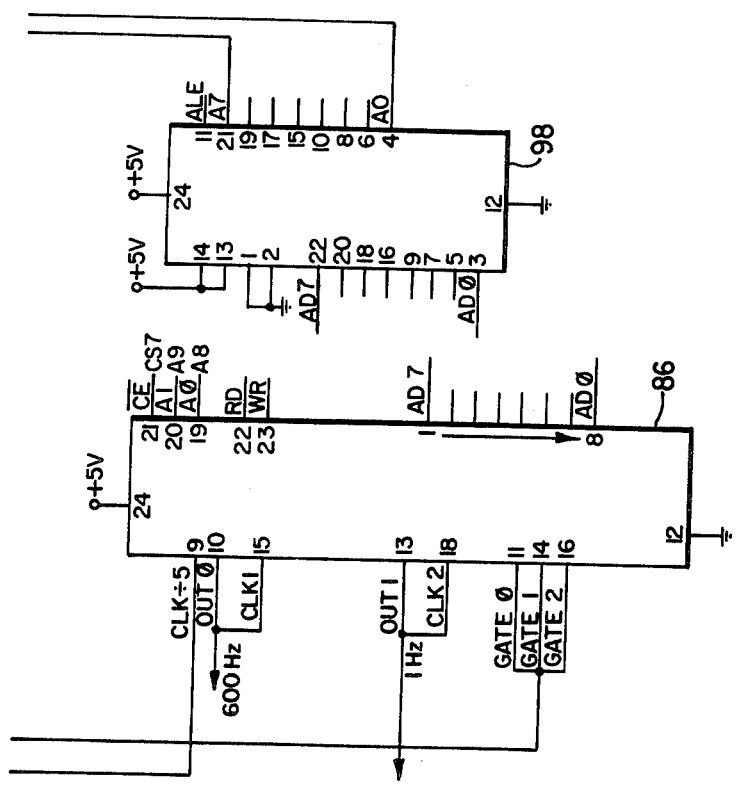
Figure 6A:
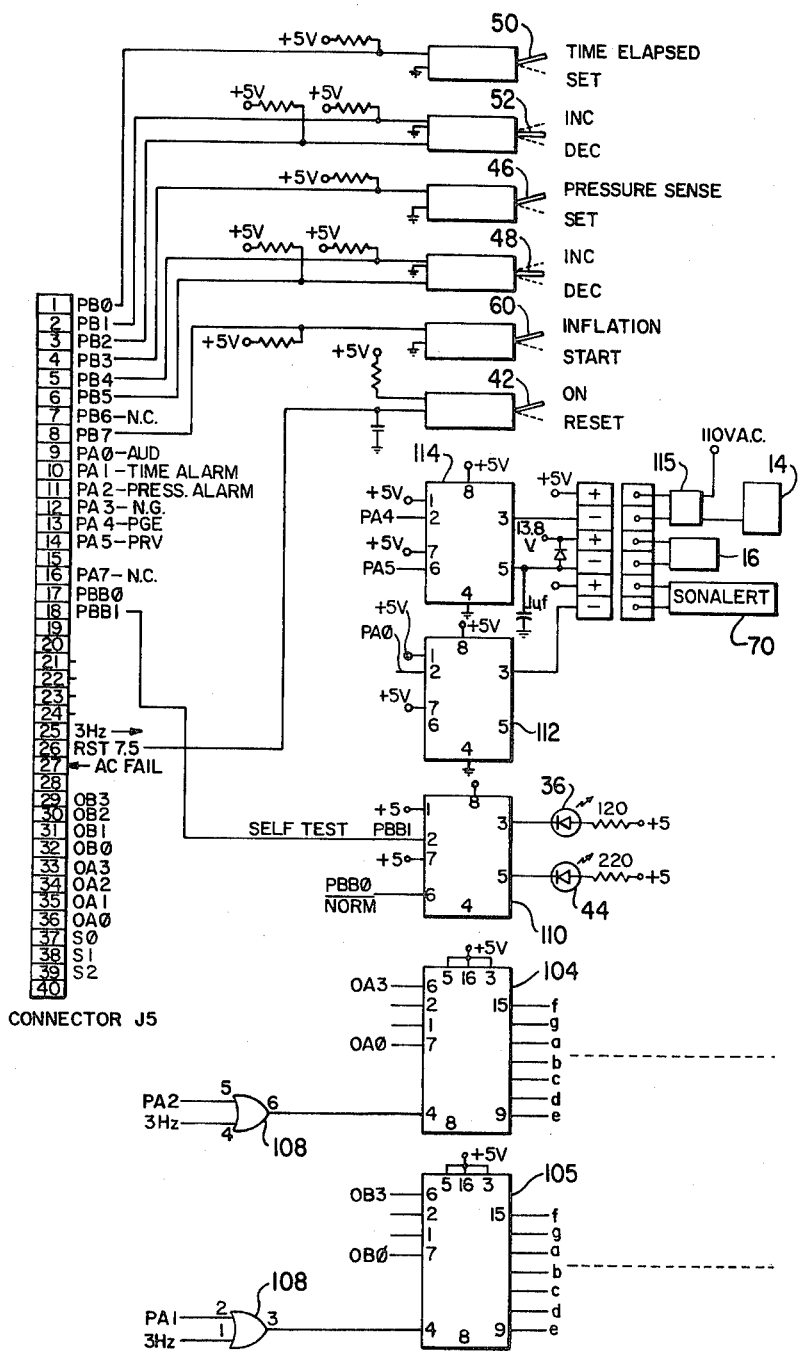
FIGS. 6A and 6B are an electronic circuit schematic diagram for the control/display circuitry of the preferred embodiment.
Figure 6B:
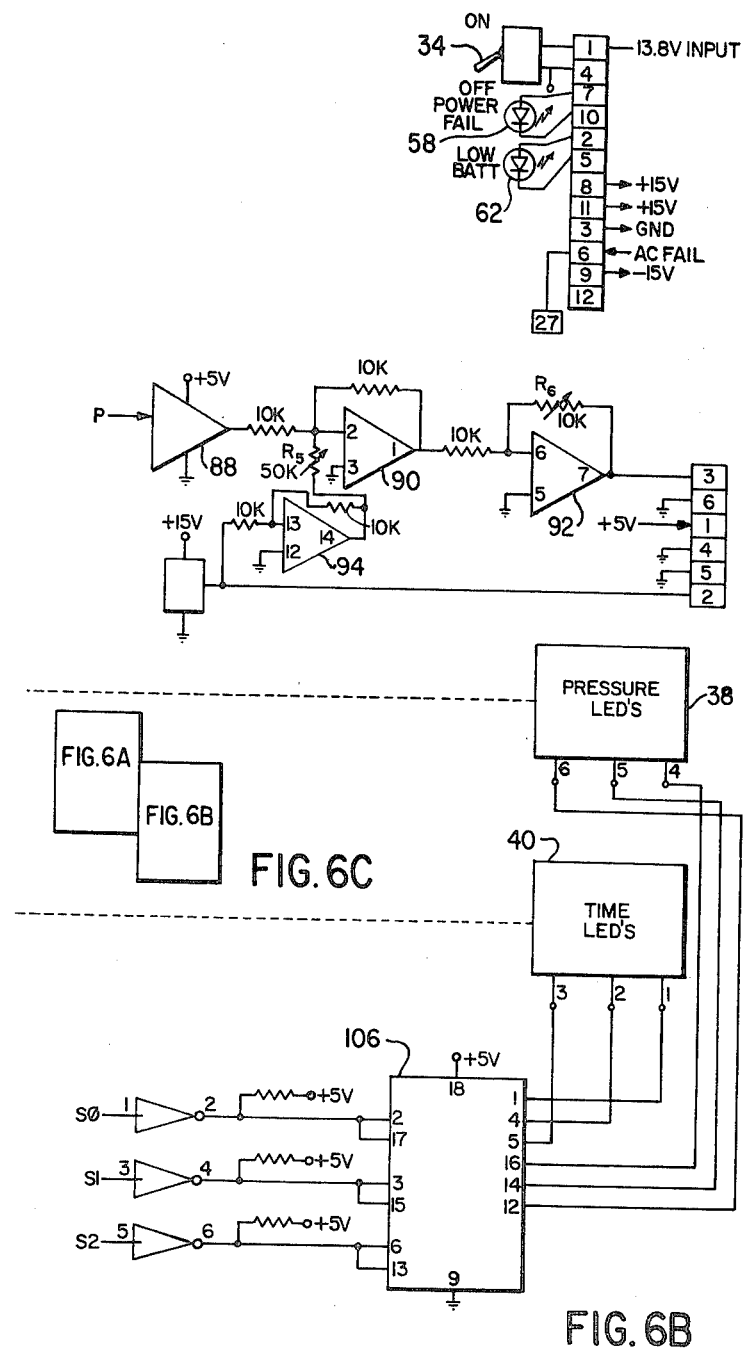

In the preferred embodiment, pressure sensing means 18 comprises a National Semiconductor LX1702GN electronic pressure transducer shown at 88 in FIG. 6B. Cuff 10 is coupled via hose 20 and port 56 (FIG. 2) to the inlet port of pressure transducer 88. Pressure transducer 88 produces an output voltage in the 2.5-12.5 volt range which corresponds to pressures of 0-760 mmHg. National Semiconductor LM324A operational amplifiers 90, 92 and 94 shift and scale the transducer output voltage into the 0-5 volt range for presentation to analog-digital converter 84 which may be seen in FIG. 5A.

For clarity of illustration, the microprocessor and its related digital circuitry are shown separately in FIGS. 5A through 5D. FIG. 5E illustrates the manner in which the circuit segments in FIGS. 5A through 5D are arranged for proper circuit interconnection. Hereinafter, FIGS. 5A through 5D are collectively referred to as "FIG. 5".

The control/display circuitry is shown in two separate FIGS. 6A and 6B. FIG. 6C illustrates the manner in which the circuit segments of FIGS. 6A and 6B are arranged for proper circuit interconnection. Hereinafter, FIGS. 6A and 6B are collectively referred to as "FIG. 6".

The pressure transducer output voltage should be calibrated after the device has been powered in the "normal" mode of operation for about 5 minutes. With a cuff pressure of 0 mmHg (achieved by disconnecting hoses 12 and 20 from cuff 10) variable resistor R5 is adjusted so that the output voltage of operational amplifier 92 is within 0.010 volts of 0.000 volts. The cuff pressure should then be increased to 300 mmHg (by using "T" adaptors to connect pressure transducer 88 to an external pressure source and to a pressure gauge having an error of less than 1%) and variable resistor R6 adjusted so that the output of operational amplifier 92 is within 0.010 volts of 1.850 volts.

(e) Microprocessor and Digital Circuitry

The microprocessor which regulates cuff pressure, drives the displays, etc. is an Intel 8085A microprocessor, shown at 78 in FIG. 5. Two TMS 2516 2K×8 bit electronically programmable read only memory ("EPROM") integrated circuits shown at 82A and 82B in FIG. 5 store the logic programs defining the sequence of operations by which microprocessor 78 controls the pneumatic tourniquet. Two Intel 8155 random access memory ("RAM") integrated circuits shown at 80A and 80B in FIG. 5 each provide 256 bytes of 8 bit "scratchpad" memory in which volatile data is stored. EPROMs 82A and 82B are defined to contain memory addresses 0000 through 07FF (hexadecimal) and 0800 through 0FFF respectively. RAMs 80A and 80B are defined to contain memory addresses 2700 through 27FF and 2800 through 28FF respectively.

Lines AD0 through AD7 are used to pass data in 8 bit format between microprocessor 78, RAMs 80A and 80B, EPROMS 82A and 82B, display interface 96 (which controls, as hereinafter described, the formatting of the pressure and time information appearing in displays 38 and 40), and timer 86 (which keeps track of elapsed time).

In order to simplify the transmission of data to and from microprocessor 78, display interface 96 and timer 86 are arbitrarily defined as comprising memory locations 3000 through 37FF and 3800 through 3FFF respectively, although they are not "memory" in the conventional sense.

Addressing information presented by microprocesor 78 on lines A11 through A15 is sufficient to identify an address within the range of addresses represented by one of EPROMs 82A or 82B, RAMs 80A or 80B, display interface 96 or timer 86. An Intel 8205 "chip select" integrated circuit 100 is connected to address lines A11 through A15. By decoding the information presented on these lines, chip select 100 is able to identify which of RAMs 80A and 80B, EPROMs 82A and 82B, display interface 96 or timer 86 is to be addressed by microprocessor 78. Output lines CS0, CS1, CS4, CS5, CS6 and CS7 of chip select 100 are used to "enable" one of EPROM 82A, EPROM 82B, RAM 80A, RAM 80B, display interface 96 or timer 86 respectively.

A National Semiconducter 74LS139 dual one-of-four decoder 102 generates additional timing commands for addressing one of EPROMs 82A or 82B. Demultiplexer 98 (which is an Intel 8212 8 bit latch integrated circuit) demultiplexes the data on lines AD0 through AD7 for presentation to either EPROM 82A or EPROM 82B.

The scaled 0–5 volt output of pressure transducer 88 is presented to analog-digital converter 84 at its input terminal "IN0". Microprocessor 78 is programmed as hereinafter described to apply appropriate signals at the "start" and "ALE" terminals of analog-digital converter 84 to cause conversion of the pressure transducer output signal from analog to digital form. The 8 bit digital result is passed from analog-digital converter 84 to input port "A" of RAM 80A for storage in the RAM.

Signals generated by front panel switches 46, 48, 50, 52 and 60 are passed via connectors J5/J6 (FIGS. 6 and 7) to input port "B" of RAM 80A for storage in the RAM. Port "B" of RAM 80A is configured to accept these signals as follows:

| INPUT LINE OF RAM 80A | SIGNAL |
| --- | --- |
| PB0 | Switch 50 Time "elapsed" or "set" |
| PB1 | Switch 52 |
| PB2 | Time "increase" or "decrease" (2 bits) |
| PB3 | Switch 46 Pressure "sensed" or "set" |
| PB4 | Switch 48 |
| PB5 | Pressure "increase" or "decrease" (2 bits) |
| PB6 | not used |
| PB7 | Switch 60 "inflation start" |

Port "C" of RAM 80A comprises a single line PCO which conveys the TTL logic "power fail" signal generated in the power supply to microprocessor 78.

RAM 80B stores information for triggering the various alarms and for activating pressurizing means 14 and pressure relief means 16. Port "A" of RAM 80B is configured to convey the following signals:

| OUTPUT LINE OF RAM 80B | SIGNAL |
| --- | --- |
| PA0 | audible alarm trigger |
| PA1 | time alarm trigger |
| PA2 | pressure alarm trigger (over or under pressurization) |
| PA3 | not used |
| PA4 | activation signal for pressurizing means 14 |
| PA5 | activation signal for pressurizing relief means 16 |
| PA6 | timer enable |
| PA7 | not used |

Port "B" of RAM 80B is configured to convey the following signals:

| OUTPUT LINE OF RAM 80B | SIGNAL |
| --- | --- |
| PBB0 | Normal Mode status signal |
| PBB1 | Self Test Mode status signal |
| PBB2–PBB7 | not used |

Display Interface 96 is an Intel 8279 display/keyboard interface controller integrated circuit which handles the formatting of information appearing in displays 38 and 40. Microprocessor 78 converts the "pressure" or "time" information to be displayed into a BCD format which is passed to display interface 96 when the address presented at microprocessor lines A11 through A15 results in the "enabling" of display interface 96 by chip select 100. The BCD digits representing "pressure" are passed on lines 0A0 through 0A3 from display interface 96 via connector J5/J6 to a National Semiconductor DS8858 BCD to 7 segment decoder/driver 104 (FIG. 6), which passes the decoded 7 segment information to display 38. The BCD digits representing "time" are passed in similar fashion on lines 0B0 through 0B3 from display interface 96 to display 40 via a second decoder/driver 105. Display interface 96 also generates an appropriate 3 bit signal on lines S0 through S2 to determine .hwich of the six individual display digits of displays 38 and 40 are to be activated. The S0–S2 signals pass through a National Semiconducter DS8863 hex inverting buffer 106 (FIG. 6) which absorbs sink current from the displays.

As mentioned above, the "time" or "pressure" displays are caused to flash on and off when a pressure or time alarm is triggered. As indicated in FIG. 6, one-half of a National Semiconductor 74LS32 quad or gate 108 is used to gate the time and pressure alarm trigger signals appearing at lines PA1 and PA2 respectively of RAM 80B with a 3 hertz clock signal for presentation to the blanking input of decoder/drivers 104 and 105 in order to flash either display upon triggering of the appropriate alarm.

The "normal" or "self test" mode status signals appearing at lines PBB0 and PBB1 respectively of RAM 80B are coupled through connectors J5/J6 to indicator lights 44 and 36 respectively via a National Semiconductor 75451 peripheral interface driver 110 as shown in FIG. 6.

The audible alarm trigger signal appearing at line PA0 of RAM 80B is coupled through connectors J5/J6 to audible alarm 70 via a similar peripheral interface driver 112 as shown in FIG. 6. Audible alarm 70 is a SONALERT TM single tone audio alarm. Switch 42 is coupled directly to one of the "interrupt" lines of microprocessor 78. When switch 42 is depressed, an interrupt is generated, causing microprocessor 78 to transfer control (as hereinafter described) to a program for temporarily disabling audible alarm 70.

The activation signals for pressurizing means 14 and pressure relief means 16 which appear at lines PA4 and PA5 respectively of RAM 80B are coupled through connectors J5/J6 via a third peripheral interface driver 114 as shown in FIG. 6. The activation signal on line PA4 is used to enable solid state relay 115 which, in turn, couples a 110 volt AC drive signal to pressurizing means 14.

A 6.144 Mhz quartz crystal oscillator 116 (FIG. 5) serves as the master clock for microprocessor 78. The clock frequency is halved by microprocessor 78 to provide a 3.072 Mhz signal at the "CLK" output of microprocessor 78 which is in turn presented to RAM 80B. An internal timer provided on RAM 80B divides the "CLK" signal frequency by five to produce a 614.4 Khz signal which is in turn presented to analog to digital converter 84 and timer 86. (The CLK frequency is divided because the integrated circuit timer used in the preferred embodiment is only able to handle signal frequencies of less than 2 Mhz). Timer 86 produces a 600 hz output signal which is presented to RAM 80A. An internal timer on RAM 80A steps the 600 hz signal down to produce a 3 hz signal which is used as described above to cause displays 38 or 40 to flash on and off if a time or pressure alarm is triggered.

IV. Software

FIGS. 7A through 7G are software flowcharts depicting the sequence of operations which microprocessor 78 is programmed to carry out. In order to simplify the discussion of the software, a detailed description of the control signals which the software produces to actuate the hardware described above is not provided. It will however be understood by those skilled in the art that, for example, in order to "illuminate self test light 36", microprocessor 78 must generate appropriate commands to produce a signal on line PBB1 of RAM 80B which may be coupled to indicator light 36 through interface 110.

Figure 7A:
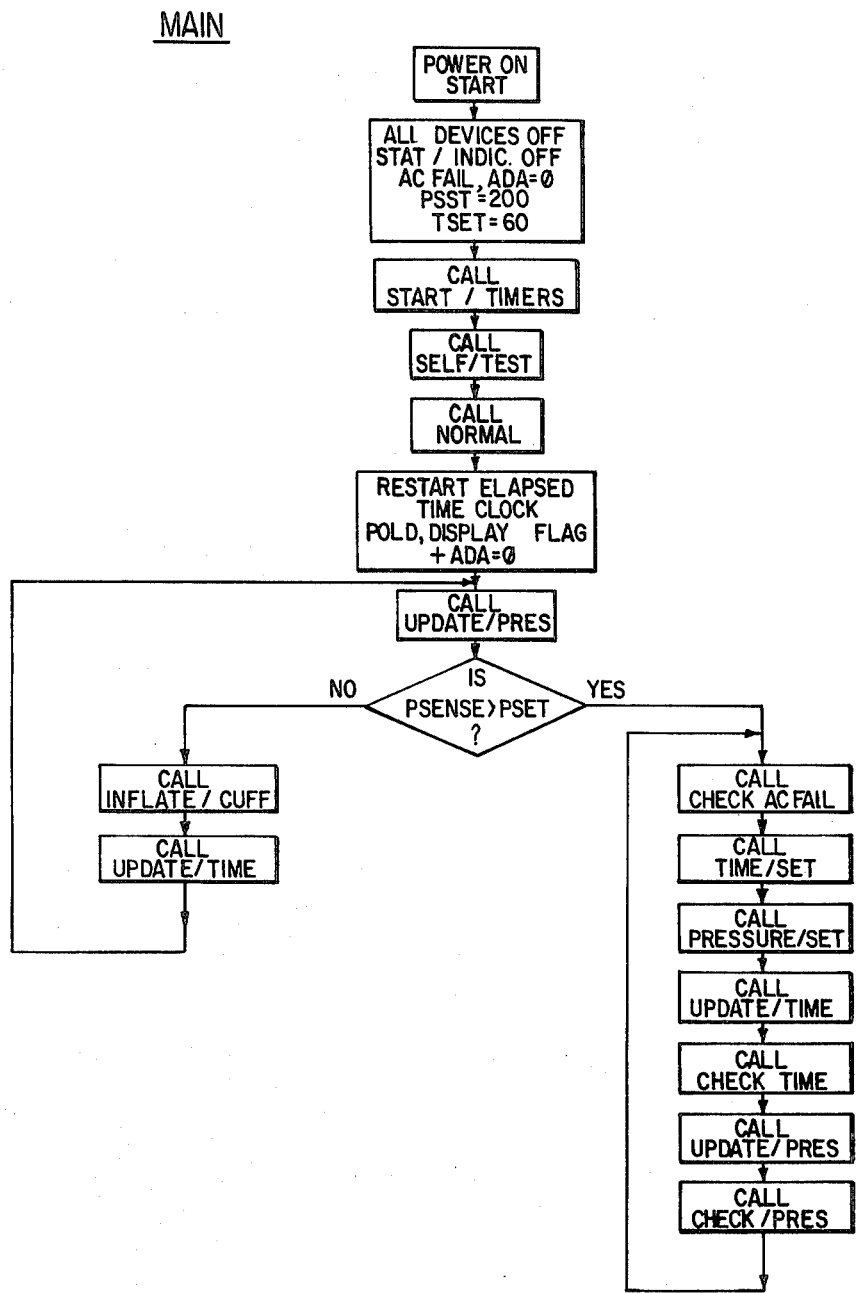
FIGS. 7A through 7G are flow charts depicting the sequence of operations for the automatic sensing and control components of the preferred embodiment of the invention.

The main control program is shown in FIG. 7A. After initializing RAMs 80A and 80B, display interface 96 and timer 86 for data transfers, control is passed to the "SELF/TEST" subroutine shown in FIG. 7B.

The SELF/TEST subroutine produces appropriate commands to illuminate self-test light 36, flash displays 36 and 40 and sound audible alarm 70 until reset switch 42 is depressed to terminate the self test sequence at which point audible alarm 70 is turned off, displays 38 and 40 are each caused to display "000" and control returns to the main program.

Figure 7B:
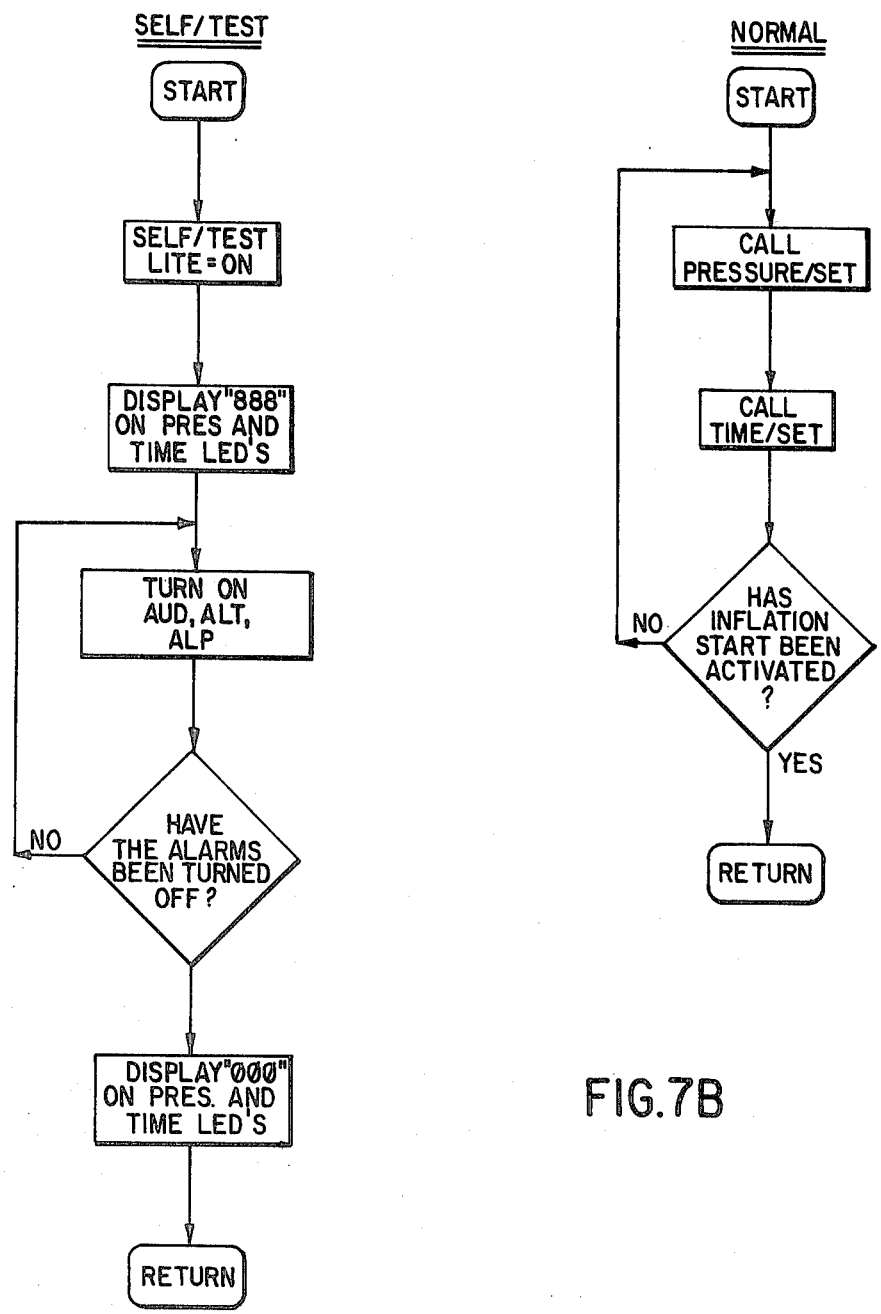
Figure 7C:
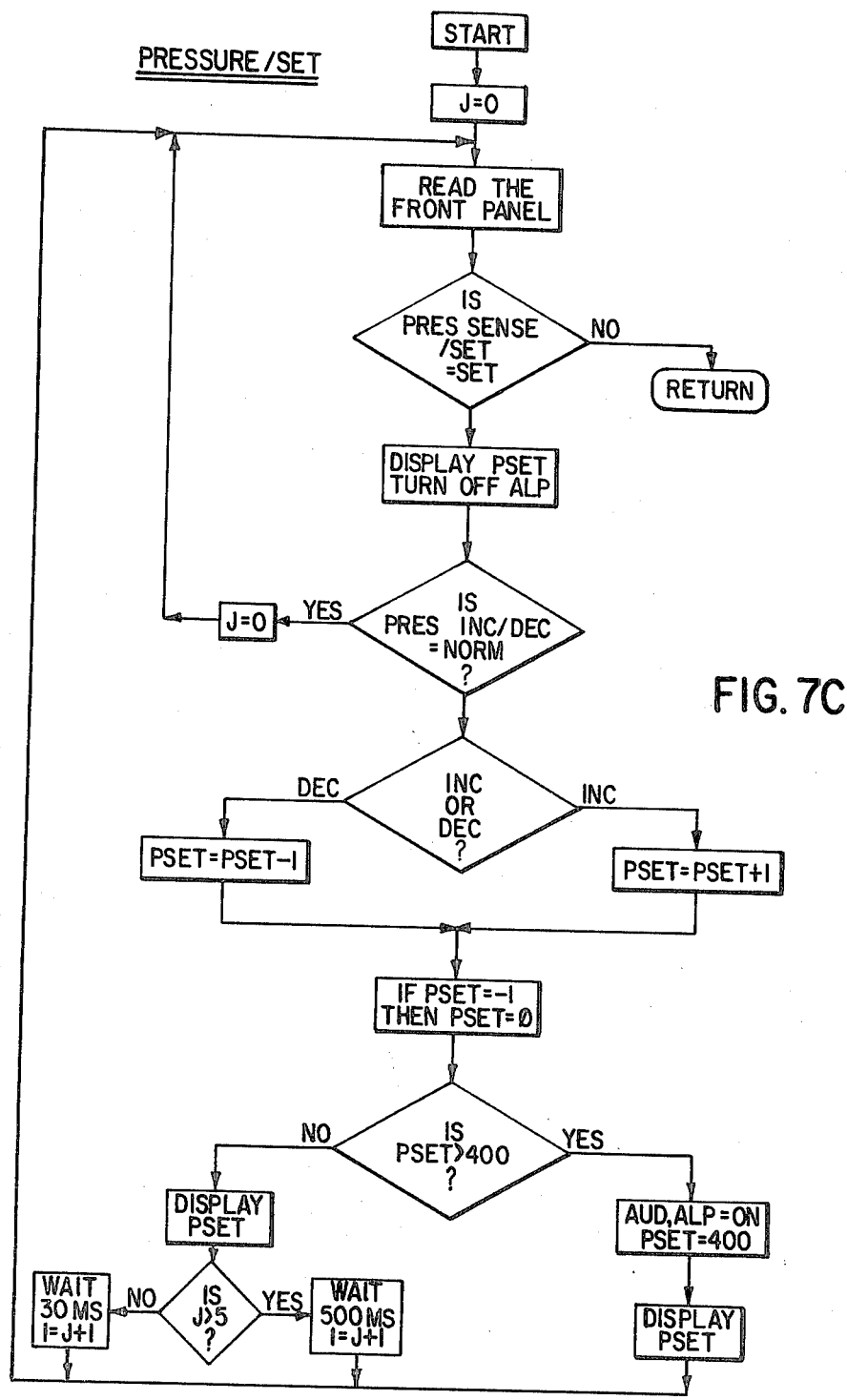
Figure 7D:
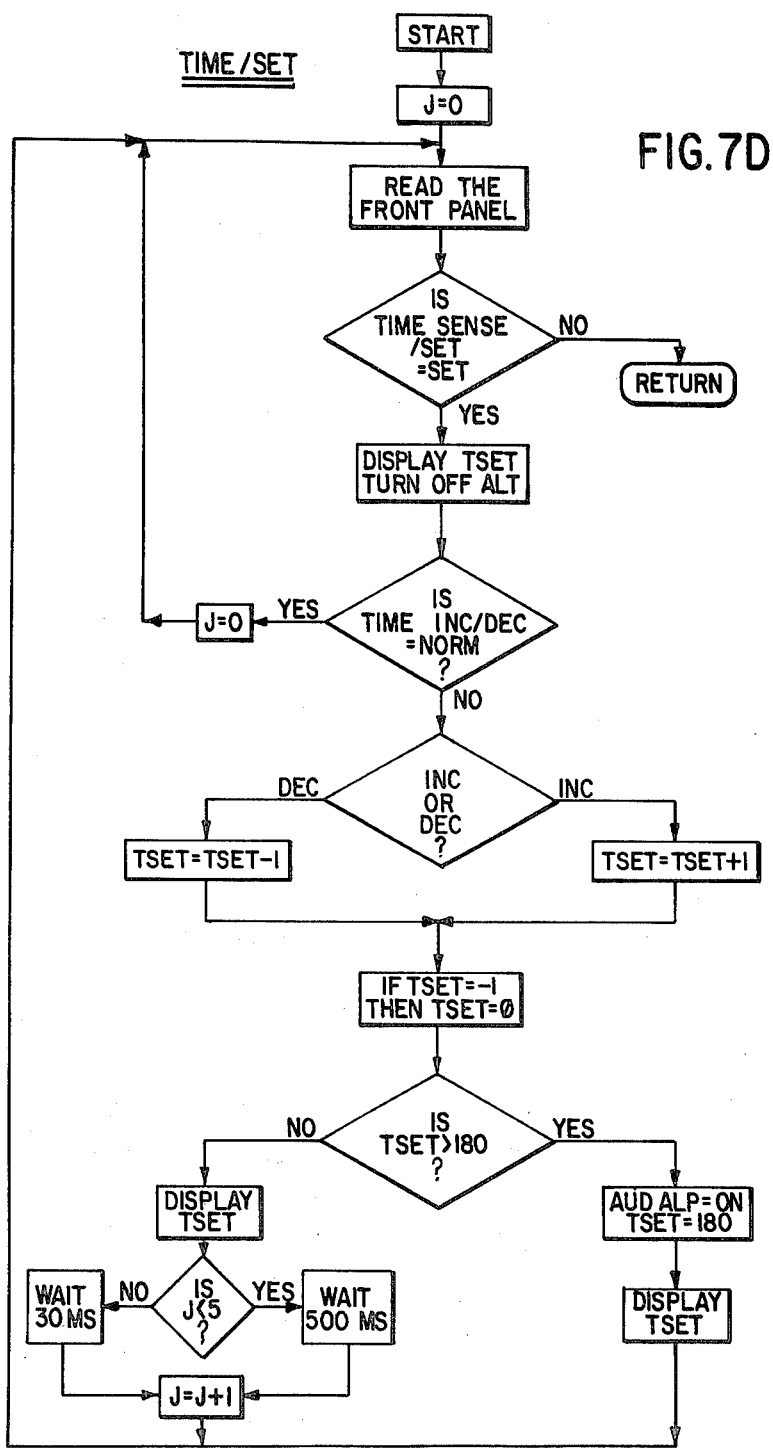
Figure 7E:
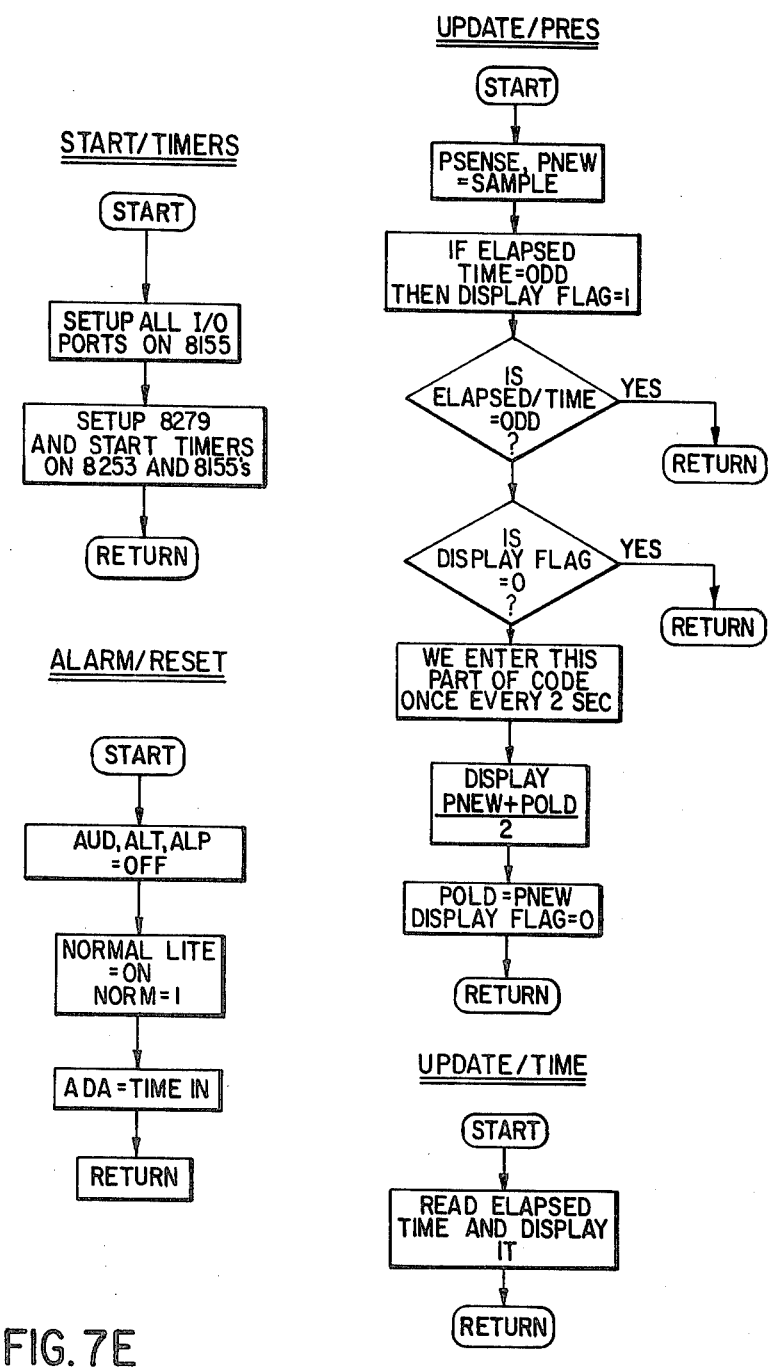
Figure 7F:
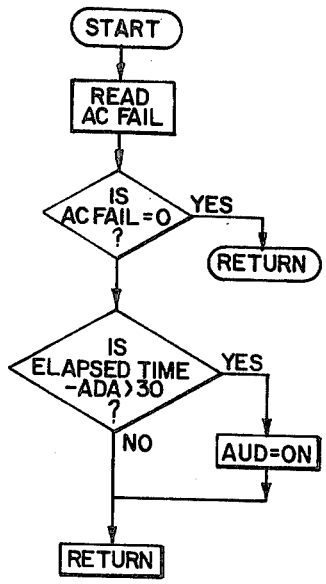
Figure 7F:
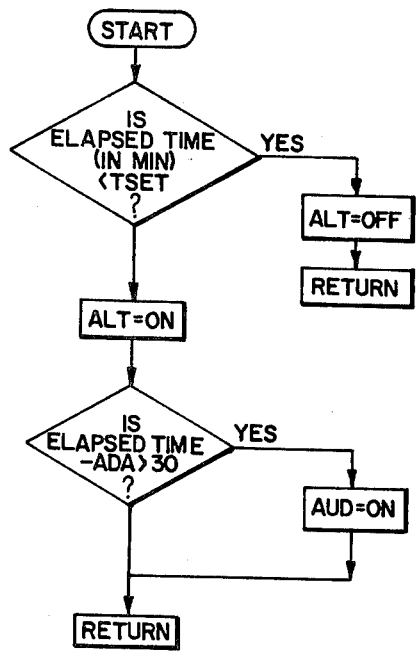
Figure 7F:
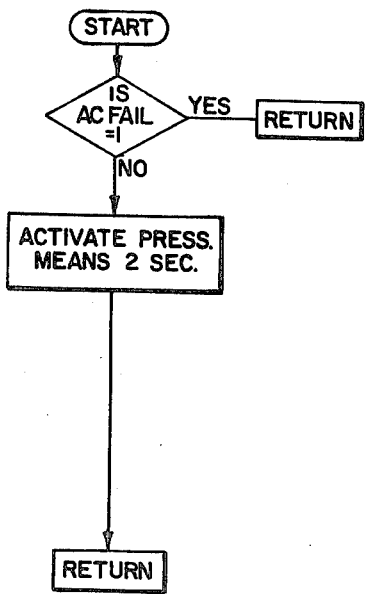

The main program next transfers control to the NORMAL subroutine shown in FIG. 7B which in turn repeatedly calls the PRESSURE/SET and TIME/SET subroutines shown in FIGS. 7C and 7D respectively until switch 60 is depressed to pressurize cuff 10, at which point control again returns to the main program.

The PRESSURE/SET subroutine simply returns control to the NORMAL subroutine unless pressure sensed/set switch 46 has been depressed to the "set" position. If switch 46 is depressed then the pressure in cuff 10 is presented in display 38. The pressure alarm trigger signal "ALP" is disabled so that a cuff under or overpressurization alarm will not be triggered while the cuff pressure is selected. The status of pressure increase/decrease switch 48 is then examined. If switch 48 is in the neutral position control returns to the beginning of the PRESSURE/SET subroutine. Otherwise, the stored value of selected presssure is incremented or decremented within the 0-400 mmHg range according to the position of switch 48. If a pressure in excess of 400 mmHg is selected then audible alarm 70 is sounded and the maximum selectable pressure of 400 mmHg caused to flash off and on in display 38. Software timers are used to delay the return of control to the beginning of the PRESSURE/SET subroutine for 0.5 seconds for the first 2.5 seconds during which switches 46 and 48 are depressed. Thereafter, control returns to the beginning of the PRESSURE/SET subroutine every 30 milliseconds. This means that the value of selected pressure changes relatively slowly (at 0.5 second intervals) for the first 2.5 seconds but changes relatively quickly thereafter which in turn provides "slow" or "fast" modes for increasing or dereasing the selected pressure.

The TIME/SET subroutine functions precisely the same as the PRESSURE/SET subroutine except the status of switches 50 and 52 are examined and the selected time caused to appear in display 40. The cuff pressurization time may be selected within a range of 0-180 minutes.

When either of switches 46 or 50 are released then the PRESSURE/SET or TIME/SET subroutine return control to the NORMAL subroutine which, as indicated above, continues to call the PRESSURE/SET and TIME/SET subroutines until switch 60 is depressed to pressurize cuff 10. When switch 60 is depressed, the NORMAL subroutine returns control to the main program. The main program then initializes some internal variables and resets an internal elapsed time counter to zero.

The main program next calls the UPDATE/PRES subroutine (FIG. 7E) which samples the pressure output of transducer 88 and then returns control to the main program unless the elapsed time counter stores an even number. This ensures that the pressure appearing in display 38 will change at no greater than two second intervals, thus providing a relatively "stable" reading for the operator. However, the pressure sensed by transducer 88 is still sampled each time the UPDATE/ PRES subroutine is entered. The value which appears in display 38 is the average of two readings taken from transducer 88 during the minimum two second display change period. Once a new value of sensed pressure has been displayed, control returns to the main program.

The main program then compares the actual cuff pressure obtained by the UPDATE/PRES subroutine from transducer 56 with the selected cuff pressure. If the actual cuff pressure is less than the selected cuff pressure, control passes to the INFLATE CUFF subroutine (FIG. 7F) which activates pressurizing means 14 for about 2 seconds. (The pressurizing means used in the preferred embodiment will increase the pressure in cuff 10 by about 9 mmHg in 2 seconds). Control is then transferred back to the main program and thence to the UPDATE/TIME subroutine (FIG. 7E) which simply reads the elapsed time from timer 96 and displays it in display 40. The UPDATE/TIME subroutine then returns control to the main program, which continues to cycle until cuff 10 is pressurized to the selected pressure.

If the actual cuff pressure is greater than the selected cuff pressure then control transfers to the CHECK ACFAIL subroutine (FIG. 7F) which triggers audible alarm 70 if the "power fail" signal has been generated by the power supply hardware. (If switch 42 is depressed a hardware interrupt is generated, causing the microprocessor to transfer control to the ALARM/ RESET subroutine (FIG. 7E) in which the current time is stored in a variable called "ADA". Before audible alarm 70 is sounded by the CHECK ACFAIL subroutine, the current time is compared with the value in variable ADA. If the difference is more than 30 seconds the alarm sounds, otherwise the audible alarm enable signal "AUD" is disabled. Switch 42 thus temporarily disables the audible alarm for a maximum of 30 seconds).

The main program then calls the TIME/SET and PRESSURE/SET subroutines to enable the operator to select new values of cuff pressurization time and pressure, in case it is desired to alter these in order to complete a medical procedure. The UPDATE/ TIME subroutine then updates the elapsed time appearing in display 40. The CHECK TIME (FIG. 7F) subroutine is then called to determine whether cuff 10 has been pressurized for, or in excess of the selected cuff pressurization time and, if so, sound audible alarm 70 and activate the time alarm signal "ALT" to flash the time in display 40. Again, the ADA variable is compared with the current time to determine whether audible alarm 70 has been temporarily deactivated.

Figure 7G:
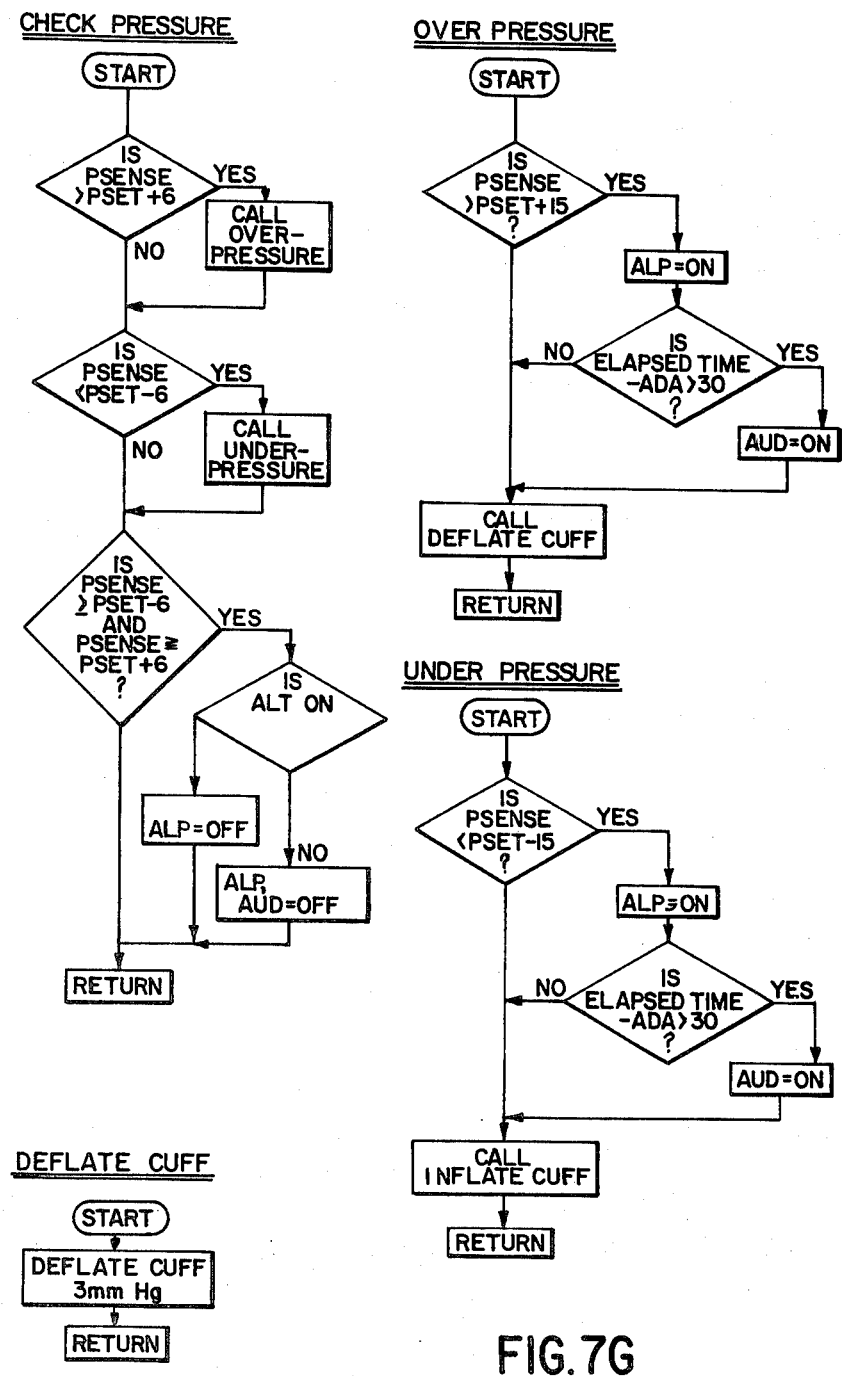

Next, the UPDATE PRESSURE subroutine is called to obtain an updated reading of the actual pressure in cuff 10 for the CHECK PRESSURE subroutine (FIG. 7G). If the actual cuff pressure exceeds the selected cuff pressure by more than 6 mmHg, the CHECK PRESSURE subroutine calls the OVER PRESSURE subroutine (FIG. 7G) which sounds audible alarm 70 (unless it has been temporarily disabled with switch 42) and flashes the pressure in display 38 if the actual cuff pressure exceeds the selected cuff pressure by more than 15 mmHg. The OVER PRESSURE subroutine also calls the DEFLATE CUFF subroutine (FIG. 7G) which activates pressure relief means 16 to lower the cuff pressure by about 3 mmHg.

If the actual cuff pressure is more than 6 mmHg below the selected cuff pressure, the CHECK PRESSURE subroutine calls the UNDER PRESSURE subroutine (FIG. 7G) to determine if the difference exceeds 15 mmHg in which case audible alarm 70 is sounded (unless it has been temporarily disabled with switch 42) and the pressure flashed in display 38. The UNDER PRESSURE subroutine also calls the INFLATE CUFF subroutine to activate pressurizing means 14 for 2 seconds and raise the cuff pressure slightly.

The main program continues to cycle by comparing the actual and selected cuff pressures and taking appropriate action as above.

I claim:
1. A pneumatic tourniquet, comprising:
an inflatable cuff;
pressurizing means for pressurizing said cuff;
pressure relief means for depressurizing said cuff;
pressure sensing means for producing a cuff pressure output signal representative of the pressure to which said cuff is pressurized;
selectable reference signal means for producing any one of a number of constant signals, each representative of a predetermined constant reference pressure;
pressure regulator means responsive to said cuff pressure output signal for selectably activating said pressurizing means and said pressure relief means to maintain said cuff pressure near a selected pressure over a time period suitably long for the performance of a surgical procedure; and
alarm means for producing a cuff over-pressurization alarm when the difference between the pressures corresponding to said cuff pressure output signal and a selected one of said constant signals exceeds a cuff over-pressurization limit.

2. A pneumatic tourniquet as defined in claim 1, wherein said pressure sensing means comprises a means for producing a digital output signal, and said pressure regulator means comprises a digital pressure regulator means responsive to said digital output signal.

3. A pneumatic tourniquet as defined in claim 2, wherein said pressurizing means comprises an electric air pump.

4. A pneumatic tourniquet as defined in claim: 1, wherein said alarm means further comprises means for producing a cuff under-pressurization alarm when the difference between the pressures corresponding to said cuff pressure output signal and said selectable reference signal exceeds a cuff under-pressurization limit.

5. A pneumatic tourniquet as defined in claim 1 wherein said cuff includes a first port for air passage into said cuff, and a second port for air passage from said cuff.

6. A pneumatic tourniquet as defined in claim 5, wherein said pressurizing means and said pressure relief means are coupled to said first port.

7. A pneumatic tourniquet as defined in claim 5 or 6 wherein said pressure sensing means is coupled to said second port.

8. A pneumatic tourniquet as defined in claim 1 further comprising alarm means for producing a power alarm upon interruption of external power supplied to said pressurizing means, said pressure relief means, said pressure sensing means, or said pressure regulator means.

9. A pneumatic tourniquet, comprising:
an inflatable cuff;
pressurizing means for pressurizing said cuff;
pressure relief means for depressurizing said cuff;
pressure sensing means for measuring and providing an output signal representative of the pressure to which said cuff is pressurized;
selectable reference pressure signal means for producing a reference signal representative of a selected reference pressure to be applied to said cuff;
pressure regulator means responsive to said reference signal for activating said pressurizing means and said pressure relief means to regulate said cuff pressure, said pressure regulator means being characterized in that it is operable to maintain said cuff pressure within a preassigned operational pressure tolerance window in association with a first selected reference pressure and to shift said pressure tolerance window in response to a change to a second selected reference pressure to maintain said cuff pressure within said pressure tolerance window in association with said second selected reference pressure.

10. A pneumatic tourniquet as defined in claim 9 which further comprises an alarm means that receives said output signal and produces a cuff over-pressurization alarm whenever the difference between the pressures corresponding to said reference signal and said output signal exceeds a preassigned over-pressurization limit.

11. A pneumatic tourniquet as defined in claim 9 which further comprises an alarm means that receives said output signal and produces a cuff under-pressurization alarm whenever the difference between the pressures corresponding to said reference signal and said output signal exceeds a preassigned under-pressurization limit.

* * * * *

REEXAMINATION CERTIFICATE (1848th)
United States Patent [19]

McEwen

[11] B1 4,469,099

[45] Certificate Issued Nov. 17, 1992

[54] PNEUMATIC TORNIQUET

[75] Inventor: James A. McEwen, Richmond, Canada

[73] Assignee: Western Clinical Engineering Ltd., Vancouver, Canada

Reexamination Request:
No. 90/002,527, Dec. 2, 1991

Reexamination Certificate for:
Patent No.: 4,469,099
Issued: Sep. 4, 1984
Appl. No.: 451,610
Filed: Dec. 20, 1982

[51] Int. Cl.[5] .................................. A61B 17/12
[52] U.S. Cl. ........................... 606/202; 128/682
[58] Field of Search ......................... 606/202, 203

[56] References Cited

U.S. PATENT DOCUMENTS

| | | |
|---|---|---|
| 3,085,599 | 4/1963 | Kronheim . |
| 3,095,873 | 7/1963 | Edmunds, Jr. . |
| 3,527,207 | 9/1970 | Gottfried . |
| 3,552,383 | 1/1971 | Krueger et al. ................ 128/682 |
| 3,633,567 | 1/1972 | Sarnoff . |
| 4,106,002 | 8/1978 | Hogue ........................ 606/202 X |
| 4,256,094 | 3/1981 | Kapp et al. . |
| 4,294,261 | 10/1981 | Baker et al. ..................... 128/691 |
| 4,321,929 | 3/1982 | Lemelson et al. .......... 606/202 X |
| 4,326,536 | 4/1982 | Kitagawa et al. . |

FOREIGN PATENT DOCUMENTS

| | | |
|---|---|---|
| 15368/70 | 11/1971 | Australia . |
| 79999/75 | 10/1976 | Australia . |
| 2477867 | 9/1980 | France . |
| 458002 | 6/1950 | Italy . |
| 40-4374 | 2/1965 | Japan . |
| 43-27689 | 11/1968 | Japan . |
| 54-120878 | 8/1979 | Japan . |
| 1253501 | 11/1971 | United Kingdom ............ 128/682 |
| 2006961 | 5/1979 | United Kingdom . |

*Primary Examiner*—Michael H. Thaler

[57] ABSTRACT

A pneumatic tourniquet includes an inflatable cuff, a pressurizing mechanism for pressurizing the cuff, a pressure relief mechanism for depressurizing the cuff, a pressure sensing mechanism for sensing the pressure to which the cuff is pressurized and a pressure regulator mechanism for selectably activating the pressurizing mechanism and the pressure relief means to maintain the cuff pressure near a selected pressure. Visual and audible alarm signals are triggered if the cuff pressure exceeds a cuff pressurization limit, if the cuff pressure falls below a cuff depressurization limit, or if the cuff has remained pressurized for, or in excess of a selected time period.

A computer may be used to sense the cuff pressure and pressurized or depressurized the cuff as required to maintain the cuff pressure within upper and lower cuff pressure limits.

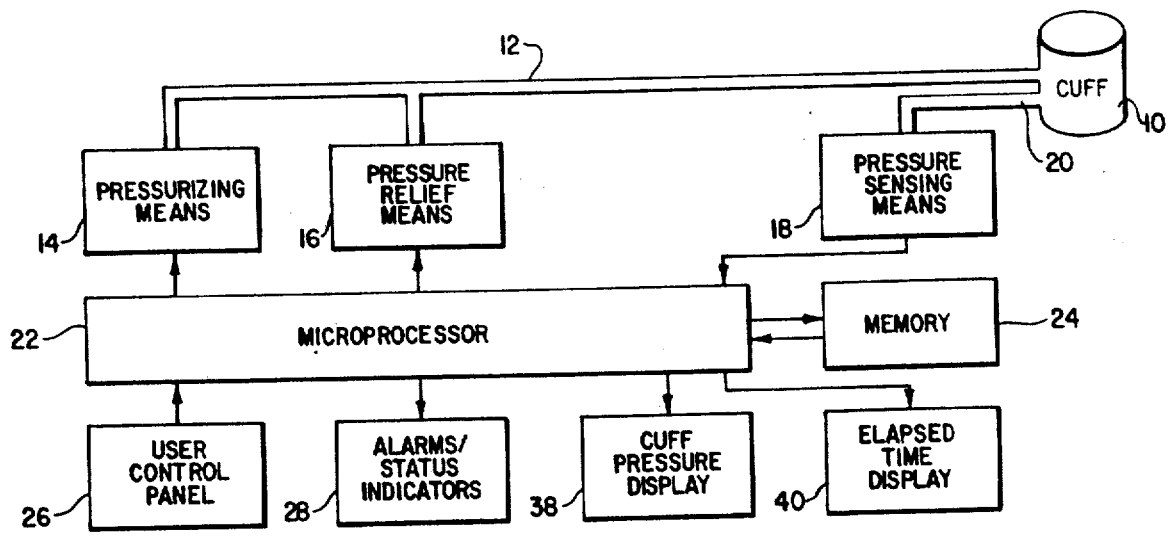

REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

The patentability of claims 1-11 is confirmed.

New claims 12-22 are added and determined to be patentable.

*12. The penumatic tourniquet of claim 1 wherein the alarm means functions such that the cuff pressure level above which the alarm is produced automatically changes in response to changes in the selection of the constant signal.*

*13. The pneumatic tourniquet of claim 1 wherein the alarm means automatically establishes the cuff pressure level above which the alarm is produced as the sum of the over-pressurization limit and the pressure corresponding to the selected one of said constant signals, irrespective of which one of the constant signals is selected.*

*14. The pneumatic torniquet of claim 4 wherein the alarm means functions such that the cuff pressure level below which the alarm is produced automatically changes in response to changes in the selection of the constant signal.*

*15. The pneumatic tourniquet of claim 4 wherein the alarm means automatically establishes the cuff pressure level below which the alarm is produced as the pressure corresponding to the selected one of said constant signals less the under-pressurization limit, irrespective of which one of the constant signals is selected.*

*16. The pneumatic tourniquet of claim 9 wherein the preassigned operational pressure tolerance window is established as a pressure range representing surgically acceptable variations in the pressure that is selected to be applied to the cuff, and wherein the pressure regulator means is operable for maintaining the cuff pressure within the range by determining the difference between the cuff pressure represented by the output signal and the selected pressure represented by the reference signal and by selectively activating the pressurizing means and the pressure relief means in a manner that permits that difference to be greater than zero but not greater than a predetermined portion of the range.*

*17. The pneumatic tourniquet of claim 16 wherein the pressure regulator means selectively activates the pressurizing means and the pressure relief means when the difference exceeds the predetermined portion of the range thereby to reduce the value of the difference to an amount less than the predetermined portion of the range while permitting that reduced difference to be greater than zero.*

*18. The pneumatic tourniquet of claim 9 wherein the pressure regulator means includes a battery that is operable for supplying electrical energy to the pressurizing means and the pressure relief means, the pressurizing means and pressure relief means consuming electrical energy supplied by the battery only when activated, and wherein the operational pressure tolerance window is preassigned to establish a pressure range representing surgically acceptable variations in the pressure that is selected to be applied to the cuff, so that the pressure regulating means does not activate the pressurizing means and the pressure relief means when variations in cuff pressure are within the range, thereby minimizing the amount of battery energy consumed by the pressurizing means and the pressure relief means during the time period the battery is operable for supplying the energy.*

*19. The pneumatic tourniquet of claim 10 wherein the alarm means functions such that the cuff pressure level above which the alarm is produced automatically changes in response to changes in the selection of the constant signal.*

*20. The pneumatic tourniquet of claim 10 wherein the alarm means automatically establishes the cuff pressure level above which the alarm is produced as the sum of the over-pressurization limit and the pressure corresponding to the selected one of said constant signals, irrespective of which one of the constant signals is selected.*

*21. The pneumatic tourniquet of claim 11 wherein the alarm means functions such that the cuff pressure level below which the alarm is produced automatically changes in response to changes in the selection of the constant signal.*

*22. The pneumatic tourniquet of claim 11 wherein the alarm means automatically establishes the cuff pressure level below which the alarm is produced as the pressure corresponding to the selected one of said constant signals less the under-pressurization limit, irrespective of which one of the constant signals is selected.*

* * * * *